(12) United States Patent
Kolkar Mohammed et al.

(10) Patent No.: US 11,598,777 B1
(45) Date of Patent: Mar. 7, 2023

(54) IMMUNO-OPTOMAGNETIC POINT-OF-CARE ASSAY AND METHOD FOR DETECTION OF ANALYTE USING MULTIFUNCTIONAL OPTOMAGNETIC QUANTUM DOT NANQCRYSTALS (MQDS)

(71) Applicant: SABANCI UNIVERSITESI NANOTEKNOLOJI ARASTIRMA VE UYGULAMA MERKEZI, Istanbul (TR)

(72) Inventors: Javed Hussain Niazi Kolkar Mohammed, Istanbul (TR); Anjum Qureshi, Istanbul (TR)

(73) Assignee: SABANCI UNIVERSITESI NANOTEKNOLOJI ARASTIRMA VE UYGULAMA MERKEZI, Istanbul (TR)

( * ) Notice: Subject to any disclaimer, the term of this patent is extended or adjusted under 35 U.S.C. 154(b) by 0 days.

(21) Appl. No.: 17/799,941

(22) PCT Filed: Feb. 17, 2020

(86) PCT No.: PCT/TR2020/050115
§ 371 (c)(1),
(2) Date: Aug. 16, 2022

(87) PCT Pub. No.: WO2021/167542
PCT Pub. Date: Aug. 26, 2021

(51) Int. Cl.
| | |
|---|---|
| *G01N 33/58* | (2006.01) |
| *G01N 33/543* | (2006.01) |
| *G01N 33/574* | (2006.01) |
| *C09K 11/02* | (2006.01) |
| *C09K 11/88* | (2006.01) |
| *B82Y 25/00* | (2011.01) |

(Continued)

(52) U.S. Cl.
CPC ...... *G01N 33/57415* (2013.01); *C09K 11/025* (2013.01); *C09K 11/883* (2013.01); *G01N 33/588* (2013.01); *B82Y 15/00* (2013.01); *B82Y 20/00* (2013.01); *B82Y 25/00* (2013.01); *G01N 2333/91205* (2013.01)

(58) Field of Classification Search
CPC .......... G01N 33/588; G01N 33/54393; G01N 33/54353
See application file for complete search history.

(56) References Cited

FOREIGN PATENT DOCUMENTS

| KR | 20190037082 A | 4/2019 |
|---|---|---|
| WO | 2010085658 A1 | 7/2010 |

OTHER PUBLICATIONS

Vineeta Panwar, et al., PEGylated magnetic nanoparticles (PEG@Fe304) as cost effective alternative for oxidative cyanation of tertiary amines via C-H activation, Applied Catalysis A: General, 2015, pp. 25-31, vol. 498.

(Continued)

*Primary Examiner* — Shafiqul Haq
(74) *Attorney, Agent, or Firm* — Bayramoglu Law Offices LLC

(57) ABSTRACT

Provided are a novel immuno-optomagnetic point-of-care (PoC) assay and in particular, a method for detecting an analyte using magnetic nanoparticles and quantum dots (QD) having antibodies which are interfaced with the fabricated PoC biochip platform for quantitative analysis, and an immuno-optomagnetic detection method. The method also relates to methods of making such a plurality of conjugated magnetic quantum dot nanoparticles, methods of detecting analytes using such a plurality of conjugated quantum dot nanoparticles.

9 Claims, 13 Drawing Sheets

(51) Int. Cl.
B82Y 20/00 (2011.01)
B82Y 15/00 (2011.01)

(56) References Cited

OTHER PUBLICATIONS

Wan Ki Bae, et al., Single-Step Synthesis of Quantum Dots with Chemical Composition Gradients, Chemistry of Materials, 2008, pp. 531-539, vol. 20, No. 2.

Yanjie Zhang, et al., Dithiocarbamates as Capping Ligands for Water-Soluble Quantum Dots, ACS Applied Materials & Interfaces, 2010, pp. 3384-3395, vol. 2, No. 11.

Fabien Dubois, et al., A Versatile Strategy for Quantum Dot Ligand Exchange, Journal of the American Chemical Society, 2007, pp. 482-483, vol. 129, No. 3.

Yue Wang, et al., Stimulated Emission and Lasing from CdSe/CdS/ZnS Core-Multi-Shell Quantum Dots by Simultaneous Three-Photon Absorption, Advanced Materials, 2014, pp. 2954-2961, vol. 26, No. 18.

Takahide Sasaki, et al., Serum HER2 levels and HER2 status in tumor cells in advanced gastric cancer patients, Japanese Journal of Clinical Oncology, 2015, pp. 43-48, vol. 45, No. 1.

Tanja Fehm, et al., Determination of HER2 status using both serum HERZ levels and circulating tumor cells in patients with recurrent breast cancer whose primary tumor was HER2 negative or of unknown HER2 status, Breast Cancer Research, 2007, pp. 1-8, vol. 9, No. 5.

Aline S.C. Fabricio, et al., Shed HER2 surrogacy evaluation in primary breast cancer patients: a study assessing tumor tissue HER2 expression at both extracellular and intracellular levels, Scandinavian Journal of Clinical and Laboratory Investigation, 2019, pp. 260-267, vol. 79, No. 4.

Soudabeh Arsalani, et al., Magnetic Fe3O4 nanoparticles coated by natural rubber latex as MRI contrast agent, Journal of Magnetism and Magnetic Materials, 2019, pp. 458-464, vol. 475.

A short guide to cancer screening Increase effectiveness, maximize benefits and minimize harm, World Health Organization Regional Office for Europe, 2018, pp. 1-45.

J. Veeraraghavan, et al., A combinatorial biomarker predicts pathologic complete response to neoadjuvant apatinib and trastuzumab without chemotherapy in patients with HER2+ breast cancer, Annals of Oncology, 2019, pp. 927-933, vol. 30, Issue 6.

Moo Hyun Lee, et al., The Significance of Serum HER2 Levels at Diagnosis on Intrinsic Subtype-Specific Outcome of Operable Breast Cancer Patients, PLOS ONE, 2016, pp. 1-11, vol. 11, No. 10.

Julia Tchou, et al., Monitoring serum HER2 levels in breast cancer patients, SpringerPlus a SpringerOpen Journal, 2015, pp. 1-7, vol. 4:237.

Priya Bhusari, et al., Development of Lu-177-trastuzumab for radioimmunotherapy of HER2 expressing breast cancer and its feasibility assessment in breast cancer patients, International Journal of Cancer, 2017, pp. 938-947, vol. 140.

Shiuh-Wen Luoh, et al., GRB7 dependent proliferation of basal-like, HER-2 positive human breast cancer cell lines is mediated in part by HER-1 signaling, Molecular Carcinogenesis, 2019, pp. 699-707, vol. 58, No. 5.

Nida Iqbal, et al., Human Epidermal Growth Factor Receptor 2 (HER2) in Cancers: Overexpression and Therapeutic Implications, Molecular Biology International, 2014, pp. 1-9, vol. 2014, Article ID 852748.

Diana P. English, et al., HER2 Expression Beyond Breast Cancer: Therapeutic Implications for Gynecologic Malignancies, Molecular Diagnosis & Therapy, 2013, pp. 85-99, vol. 17 No.2.

Zhenhua Chen, et al., Ultrasensitive Sensor Using Quantum Dots-Doped Polystyrene Nanospheres for Clinical Diagnostics of Low-Volume Serum Samples, Analytical Chemistry, 2019, pp. 5777-5785, vol. 91.

Xue Qiu, et al., Nanobodies and Antibodies for Duplexed EGFR/HER2 Immunoassays Using Terbium-to-Quantum Dot FRET, Chemistry of Materials, 2016, pp. 8256-8267, vol. 28, No. 22.

Christina M. Tyrakowski, et al., Ratiometric CdSe/ZnS Quantum Dot Protein Sensor, Analytical Chemistry, 2014, pp. 2380-2386, vol. 86, No. 5.

Rumiana Bakalova, et al., Quantum Dot-Based Western Blot Technology for Ultrasensitive Detection of Tracer Proteins, Journal of the American Chemical Society, 2005, pp. 9328-9329, vol. 127, No. 26.

Regina Bilan, et al., Quantum-dot-based suspension microarray for multiplex detection of lung cancer markers preclinical validation and comparison with the Luminex xMAP® system, Scientific Reports, 2017, pp. 1-10, 7:44668.

Regina S. Bilan, et al., Engineering of Optically Encoded Microbeads with FRET-Free Spatially Separated Quantum-Dot Layers for Multiplexed Assays, ChemPhysChem, 2017, pp. 970-979, vol. 18, No. 8.

Laura Anfossi, et al., A lateral flow immunoassay for straightforward determination of fumonisin mycotoxins based on the quenching of the fluorescence of CdSe/ZnS quantum dots by gold and silver nanoparticles, Microchimica Acta, 2018, pp. 1-10, vol. 185:94.

Zhenzhen Lin, et al., Optical transformation of a CdTe quantum dot-based paper sensor for a visual fluorescence immunoassay induced by dissolved silver ions, Journal of Materials Chemistry B, 2017, pp. 826-833, vol. 5.

Zhenli Qiu, et al., Bioresponsive Release System for Visual Fluorescence Detection of Carcinoembryonic Antigen from Mesoporous Silica Nanocontainers Mediated Optical Color on Quantum Dot-Enzyme-Impregnated Paper, Analytical Chemistry, 2017, pp. 5152-5160, vol. 89.

Minoru Miyashita, et al., Quantitative diagnosis of HER2 protein expressing breast cancer by single-particle quantum dot imaging. Cancer Medicine, 2016, pp. 2813-2824, vol. 5, No. 10.

Shuo Wang, et al., Quantitative detection of the tumor-associated antigen large external antigen in colorectal cancer tissues and cells using quantum dot probe. International Journal of Nanomedicine, 2016, pp. 235-247, vol. 11.

Xue-Qin Yang, et al., Quantum dot-based quantitative immunofluorescence detection and spectrum analysis of epidermal growth factor receptor in breast cancer tissue arrays, International Journal of Nanomedicine, 2011, pp. 2265-2273, vol. 6.

Zhongliang Hu, et al., Biomarker quantification by multiplexed quantum dot technology for predicting lymph node metastasis and prognosis in head and neck cancer, Oncotarget, 2016, pp. 44676-44685, vol. 7, No. 28.

Mei Hu, et al., Ultrasensitive, Multiplexed Detection of Cancer Biomarkers Directly in Serum by Using a Quantum Dot-Based Microfluidic Protein Chip, ACS Nano, 2010, pp. 488-494, vol. 4, No. 1.

Li-Juan Zhang, et al., Quantum Dot Based Biotracking and Biodetection, Analytical Chemistry, 2019, pp. 532-547, vol. 91.

Hongyan Shen, et al., Poly(ethylene glycol) Carbodiimide Coupling Reagents for the Biological and Chemical Functionalization of Water-Soluble Nanoparticles, ACS Nano, 2009, pp. 915-923, vol. 3, No. 4.

Preston T. Snee, The Role of Colloidal Stability and Charge in Functionalization of Aqueous Quantum Dots, Accounts of Chemical Research, 2018, pp. 2949-2956, vol. 51.

Kalpesh D. Mahajan, et al., Magnetic quantum dots in biotechnology—synthesis and applications, Biotechnology Journal, 2013, pp. 1424-1434, vol. 8.

Chloe Kim, et al., Integrated Magnetic Bead-Quantum Dot Immunoassay for Malaria Detection, ACS Sensors, 2017, pp. 766-772, vol. 2.

Zongbao Chen, et al., Novel electrochemical immunoassay for human IgG1 using metal sulfide quantum dot-doped bovine serum albumin microspheres on antibody-functionalized magnetic beads, Analytica Chimica Acta, 2017, pp. 24-30, vol. 979.

Maria Gazouli, et al., Development of a quantum-dot-labelled magnetic immunoassay method for circulating colorectal cancer cell detection, World Journal of Gastroenterology, 2012, pp. 4419-4426, vol. 18, Issue 32.

(56) References Cited

OTHER PUBLICATIONS

Dianping Tang, et al., Multiplexed electrochemical immunoassay of biomarkers using metal sulfide quantum dot nanolabels and trifunctionalized magnetic beads, Biosensors and Bioelectronics, 2013, pp. 37-43, vol. 46.

Hong Wang, et al., Rapid, Sensitive, and Simultaneous Detection of Three Foodborne Pathogens Using Magnetic Nanobead-Based Immunoseparation and Quantum Dot-Based Multiplex Immunoassay, Journal of Food Protection, 2011, pp. 2039-2047, vol. 74, No. 12.

Fei Yu, et al., Magnetic immunoassay using CdSe/ZnS quantum dots as fluorescent probes to detect the level of DNA methyltransferase I in human serum sample, International Journal of Nanomedicine, 2018, pp. 429-437, vol. 13.

Chloe Kim, et al., Magnetic bead-quantum dot assay for detection of a biomarker for traumatic brain injury, Nanoscale, 2015, pp. 17820-17826, vol. 7.

Ajay Kumar Gupta, et al., Synthesis and surface engineering of iron oxide nanoparticles for biomedical applications, Biomaterials, 2005, pp. 3995-4021, vol. 26.

Qiang Ma, et al., Multilayered, core/shell nanoprobes based on magnetic ferric oxide particles and quantum dots for multimodality imaging of breast cancer tumors, Biomaterials, 2012, pp. 8486-8494, vol. 33.

Gang Ruan, et al., Simultaneous Magnetic Manipulation and Fluorescent Tracking of Multiple Individual Hybrid Nanostructures, Nano Letters, 2010, pp. 2220-2224, vol. 10.

Kalpesh D. Mahajan, et al., A MagDot-Nanoconveyor Assay Detects and Isolates Molecular Biomarkers, Chemical Engineering Progress, 2012, pp. 41-46, vol. 108.

Craig Tuerk, et al., Systematic Evolution of Ligands by Exponential Enrichment: RNA Ligands to Bacteriophage T4 DNA Polymerase, Science, 1990, pp. 505-510, vol. 249.

Zhen Rong, et al., Dual-color magnetic-quantum dot nanobeads as versatile fluorescent probes in test strip for simultaneous point-of-care detection of free and complexed prostate-specific antigen, Biosensors and Bioelectronics, 2019, pp. 1-8, vol. 145:111719.

Anjum Qureshi, et al., CdSe/CdS/ZnS nanocrystals decorated with $Fe_3O_4$ nanoparticles for point-of-care optomagnetic detection of cancer biomarker in serum, Sensors & Actuators: B: Chemical, 2020, pp. 1-9, vol. 321:128431.

BOROFLOAT 33—Borosilicate glass, 2020, pp. 1-3, retrieved from: https://www.us.schott.com/borofloat/english/index.html.

US 11,598,777 B1

IMMUNO-OPTOMAGNETIC POINT-OF-CARE ASSAY AND METHOD FOR DETECTION OF ANALYTE USING MULTIFUNCTIONAL OPTOMAGNETIC QUANTUM DOT NANQCRYSTALS (MQDS)

CROSS REFERENCE TO THE RELATED APPLICATIONS

This application is the national stage entry of International Application No. PCT/TR2020/050115, filed on Feb. 17, 2020, the entire contents of which are incorporated herein by reference.

TECHNICAL FIELD

The present invention relates to a versatile, rapid and cost-effective immuno-optomagnetic point-of-care (PoC) assay. More particularly, the present invention relates to a method for detecting a bioanalyte, eg., disease biomarkers, using magnetic quantum dots (MQDs) having antibodies which are interfaced with the fabricated PoC biochip platform for quantitative analysis, and an immuno-optomagnetic detection method.

BACKGROUND

Development of nano-biosensors as a point-of-care (PoC) diagnostics device is a most promising approach for early, sensitive, rapid and cost-effective analysis for health and well-being or monitoring recurring diseases, such as cancers. Existing methods for the diagnosis of cancer are highly expensive and time-consuming. Most common among such methods are mammogram, tissue biopsy tests, ELISA tests, PET/CAT scans that makes rapid diagnosis extremely difficult and time-consuming.

Among many different types of cancers, breast cancer is the most common cancer among women and it is regarded as the second leading cause of cancer related mortality worldwide [10]. It is estimated that 2.09 million breast cancer related cases were estimated to have occurred causing 627,000 deaths worldwide according to a WHO 2018 report. These figures account for about 15% of all cancer deaths among women [10].

Major concerns for a progressive cancer disease is its undetectability at the early stages of development, or lack of a rapid, less-expensive point-of-care based early diagnostic tool, which could provide early warning signs that pave way to seek medical attention and enable prevention of a progressive cancer.

Human epidermal growth factor receptor 2 (ErbB2/Her2) protein is associated with multiple cancer types, including in breast cancer, it is found to be overexpressed by 15-30% and 10-30% in gastric/gastroesophageal cancers and thus it serves as a prognostic and predictive biomarker [16]. The extracellular ErbB2/Her2 cleaved protein from tumor cells enters the blood stream as a result of increased expression of ErbB2/Her2 which serves as an indicator of a high risk of cancer disease. The clinical prognostic and predictive usefulness of the serum ErbB2/Her2 levels is warranted for clinic-pathologic parameters and therapy monitoring marker [6, 11, 12, 16]. It is imperative to monitor ErbB2/Her2 protein levels because it is also found overexpressed in other types of cancers including ovarian, lung, colorectal, bladder, pancreatic, colon, endometrial and oral cancers [16, 17].

Breast cancer patients' blood samples contains elevated levels of ErbB2/Her2 protein concentrations (15-75 ng $mL^{-1}$) compared to 2-15 ng $mL^{-1}$ of same protein observed in normal individuals [6-8]. Early detection and monitoring of the serum ErbB2/Her2 levels can increase the diagnosis speed, screening and successful treatment of cancer disease, and survival of the patient. Therefore, there is an urgent demand for a sensitive, rapid and accurate technology platform for PoC based detection of cancer biomarker in serum, tissue or body fluids.

A number of conventional and well-established diagnostic methods are currently in practice, such as fluorescence insitu hybridization (FISH) [6, 11, 12], enzyme-linked immunosorbent assay (ELISA) [7, 13], radioimmunoassay [14], and chemiluminescence immunoassays [6, 8, 15].

There are several major problems with the existing above mentioned techniques including their high-cost and time-consuming that prevents repetitive testing, required sophisticated instruments, and trained personal to perform the tests, which makes such approaches more complicated and unsuitable for early detection of cancer disease. Moreover, all these existing diagnostic approaches require laborious washing steps in order to separate unbound and labeling of free ligands/receptors to minimize their non-specific fluorescent background signal and complex matrix susceptibility. These parameters affect the stability and structure of target probe biomolecule specificity and weaken the sensitivity of immunoassay platform.

Despite of the existing diagnostic methods that most of them have been around for the past decade, none of them have been successfully implicated for early cancer diagnosis. Taking all the above into consideration, it is time to develop and evaluate new diagnostic approaches that at least accessible, cost-effective, and affordable PoC based diagnosis, which paves way to prevention from progression of cancer and treatment. Extension of traditional diagnostic approaches into lab-on-a chip and PoC diagnostics currently presents significant challenges, especially when affordability, speed and accuracy of detection of analytes, such as diagnosis of cancers or other chronic diseases that are not limited to it, but can also be applicable to a whole range of other targets, including other biomarkers, bacterial/viral infections, nucleic acids (DNA/RNA), drugs, chemicals, pesticides or environmental agents.

Semiconductor quantum dot (QD) nanocrystals (2-10 nm in size range) have unique size-dependent properties with dimensional similarities with biological macromolecules making them most suitable for optical biosensors and biological imaging. QDs' emission can be tuned by their size and composition that has broad excitation and absorption ranges, narrow and symmetrical photo emission and strong luminescence and robust photo-stability. QD-based bio-conjugates have been used as FRET diagnostic probes [18-20], western blotting [21], microbeads labeled-microarrays [22, 23], QD fluorescence quenching assays [24-26] and other QD-based immunochemistry assays [27-31] for the detection for cancer protein disease biomarker [32].

Most of the QDs-based biosensor systems suffer due to their physical or chemical instability in biological assays, but several attempts have been made to improve QDs' physico-chemical stability [32, 33], However, fabrication of QD-based bio-conjugations for biosensing application is a challenging process because of their irreversible precipitation that causes quenching that affect sensitivity [32, 34].

Recently, bio-conjugation strategies with quantum dots (QDs), magnetic microbeads and other nanoparticles have been developed for biological imaging, medical nano-diagnostics, treatment, and drug delivery systems [35, 36]. A few studies have shown the combination of large magnetic microbeads and QDs were individually functionalized with antibodies, respectively and later sandwiched with a specific target protein for detection, but it required that pure QDs be cleaved in solution phase or added separately in order to obtain a detectable signal [37-42]. Such methods although have advantages of easy separation, collection, and filtration of the probes, but require laboratory settings for assays that are not desirable or unsuitable for PoC in resource limited settings [43]. Nanosized magnetic iron oxide ($Fe_3O_4$) nanoparticles (MNPs) been successfully used in magnetically activated cell separations and single molecule manipulation that have been approved by FDA for use in magnetic resonance (MR) imaging [35].

MNPs having 5-15 nm sizes exhibit paramagnetic characteristics in solution that substantially restrict their potential aggregation [44]. Chemical combination of QDs and MNPs provide multimodal functionality that has major advantages in bio-labeling and MR imaging because of their combined optical and magnetic (optomagnetic) properties exhibited in a single nanomaterial, which enable simultaneously bio-labeling, imaging, sorting and separation processes [35, 45].

Only few reports have been focused on fabrication of magnetic QDs (MQDs) and their utility in PoC or lab-on-a-chip platforms. For eg., magnetic QDs have been used for the detection and separation of cells and biomarkers based on complimentary engineered DNA/RNA sequences [43, 46-48]. These magnetic QDs nanoprobes utilized in immunoassays were mainly fabricated by high temperature precursor decomposition, doping (transition metal doped into a bulk QDs), encapsulation (MNPs and QDs encapsulated using silica or polymer matrix) and cross-linking (MNPs and QDs conjugation by a linker or electrostatic force) methods.

The first three approaches mentioned above are limited because of loss of magnetic property due to disordered magnetic crystal structure, interfacial instability of available doped material and NP aggregation, and difficulty with sequential synthesis procedures, respectively. Among these strategies, fabricating MQDs via QD crystallization followed by MNPs crosslinking approach is fast, simple and prevents from many of the limitations of sequential synthesis steps and robustly allow interfacing with PoC immunoassay diagnostic chip.

A bio platform/kit comprising magnetic beads which contain quantum dot doped nanoparticles and sandwich assay structure that performs biological detection by attached antibodies on the magnetic beads' surface is described in KR2019037082A. This nanoparticle (silica)/quantum dot complex has inorganic material core and a quantum dot layered shell. The kit contains nitrocellulose (NS) membrane with surface-fixed quantum dot-doped nanoparticles which acts as sensing membrane.

However, in the above mentioned patent document, UV-vis spectrometer is required for detecting fluorescent signal and a Lateral Flow membrane is used for separation of materials that is not only a time-consuming process, but also accompanies the drawbacks of non-specificity and impeding sample migration to receptor interaction area on membrane. Relying on nitrocellulose membrane in the same assay process is another disadvantage because of non-specific adsorption, which results in yielding high possibility of false-positive or false-negative outcomes. Moreover, large size variation of complex silica core (120 nm) coated with multilayer quantum dots of varying sizes forms a thick shell of 20-500 nm makes it extremely uncontrollable in its particle behavior, which is undesirable for biosensing applications.

The assay kit/method presented in KR2019037082A requires complex laboratory settings and laboratory equipment to perform the tests. In addition, the assay in KR2019037082A also relies on many consumables, such as a glass plate, polystyrene 96-well microtiter plate in addition to large macro silica particles coated with multilayered QDs. Multilayer quantum dot array with silica core is independent of magnetic micro-bead that independently react with biological material (target) makes it more complicated process for sensing application.

Nitrocellulose membranes are used in lateral flow assays (LFAs) such as those in Pregnancy Test Strips, where it is useful for only qualitative YES or NO type of results. This is because, the sample in which the target molecule to be detected is first mixed with nanoparticles. As mentioned in KR2019037082A, the core silica coated with multi-layered QDs makes its size to attain as large as <120 nm and that has to travel through the nitrocellulose membrane. This has major technical problem because such a large particle size may often fail to migrate without leaving its traces in the nitrocellulose membrane. Imagining these large sizes of particles has to bind to even larger magnetic micro bead (4 micron size or 4000 nm) to form a complex as explained in the KR2019037082A. This huge complex is applied to bioactivated nitrocellulose membrane to detect/sense the target as explained in the KR2019037082A document.

In a recent study, magnetic QDs have been used for the lateral-flow immunoassay (LFIA) that utilizes over 140 nm large magnetic particles (located in the center) coated with QDs, and a smartphone assisted detection of prostate specific antigen (PSA) has been reported [49]. MNPs being in the center with QDs around it causes quenching and toxicity because of Cd in CdSe/ZnS quantum dots nanocrystals. Therefore, usage of this type of magnetic QDs is not appropriate to be kept in contact with living cells or used in-vivo. In the said study, magnetic nanobeads of 140 nm size were conjugated with QDs that further increases the size of these particles to over 150 nm. These large magnetic nanobeads are coated with QDs which makes QDs more vulnerable to interact with surrounding external environments or easily dissociate from the particle surface that negatively affects the biosensing process, or causing severe and direct cytotoxicity.

In addition, usage of LFIA-like methods mentioned above rely heavily on migration of nanoparticles in a complex matrix that are more prone to non-specific binding with LFIA matrix. This hampers the detection process using LFIA due to high possibility of false-positive/negative responses, which make such devices unsuitable for PoC settings. Therefore, direct use of smaller nano-sized magnetic nanoparticles (MNPs) on inert surfaces, as well as, fabricating a different orientation of QD-to-MNPs architectures could provide more sensitive, accurate, specific, selective, and more reliable detection of analytes in PoC settings.

SUMMARY

Broadly, the present invention provides materials and methods for sensitive detection of analytes in real serum sample for visible detection of signal within 30 min of sample application. In particular, the present invention provides multi-functional immuno-optomagnetic quantum dot (QD) nanocrystals and a fabricated PoC biochip platform.

The present invention provides a chemically synthesized and characterized optomagnetic QD nanocrystals comprising a core of QD, wherein the magnetic nanoparticles are decorated around QDs. Optomagnetic QD nanocrystals are bioactivated with analyte specific reagent, for example with antibodies (second analyte specific reagent (Ab2)) that give rise to immuno-optomagnetic nanocrystals (MQDs-Ab2). The primary (Ab1) or a second (Ab2) antibody in this invention is not limited to a single protein biomarker or disease but also possibly extended to a variety of biomolecules, receptors, pathogenic bacteria, virus, DNA/RNA, environmental contaminants, pesticides or drugs which are generally described as analyte specific reagents in the present invention. In one example, human-ErbB2/Her2 biomarker protein is demonstrated but is not limited to one disease biomarker or disease condition.

The MQDs-Ab2 in this invention provides multimodal functionality that comprised of; (a) bio-recognition and capturing of biomarker from serum, (b) magnetic separation to concentrate or isolate biomarker from bulk and dilute serum, and (c) visible detection of immuno-optomagnetic signal from MQD nanocrystals-second analyte specific reagent-target analyte complex, more specifically MQDs-Ab2-analyte complex captured on PoC biochip. The PoC biochip platform is fabricated with a glass substrate patterned with an array of immuno-reaction spots carrying Ab1 to which the MQDs-Ab2-analyte complex is sandwiched. The signal from this sandwiched-complex on PoC biochip platform can be visualized with a naked human eye by simply flashing PoC biochip surface with a UV-torch. Both Ab2 (second antibody) and Ab1 (primary antibody) binds directly to the same analyte, but each binds from a different side (different epitope) of the same analyte. First, MQD-Ab2 binds to analyte and the exposed face of the same analyte (in MQD-Ab2-analyte complex) is presented to Ab1 on PoC biochip platform to capture. In this invention, binding of primary and second antibody to the same antigen occur at different sides or different epitopes of the same analyte.

Nitrocellulose membrane used in prior art has several disadvantages, including its non-specific adsorption or blocking reaction due to its binding to non-specific molecules within the same sample. Whereas the glass substrate is more inert, where the reaction takes place providing more specificity and no non-specific adsorption as compared to any membranes. Therefore, highly specific-adsorption can occur on bio-activated glass substrates than that of nitrocellulose membranes.

Other features include: a) It is easy to spot target analyte sample on glass chip instead of nitrocellulose membrane; b) Non-specific adsorption of protein is minimal on glass chip than on nitrocellulose membrane; c) A glass chip substrate functionalized with protein is more stable and durable compared to that of a nitrocellulose membrane as substrate.

In one example, the invention provides an immuno-optomagnetic PoC assay which is designed to offer sensitive and specific signal to serum hErbB2/Her2 cancer biomarker but not limited to it, and it can also be applied to other cancer biomarkers with a detection limit of 0.62-10 ng mL$^{-1}$, which is sufficient to clinically discriminate the normal and risk-levels in patient serum. The signal detection can be made within 30 min of sample drawing from the patient to immuno-optomagnetic PoC testing, with the capability of detecting concentrations well below the clinical cutoff values.

The present invention of immuno-optomagnetic PoC assay, method has advantages of speed, sensitivity, low cost and that it does not require additional equipment or trained personnel. Thus, the present invention provides an easy-to-use, real-time and rapid cancer screening tool, which pave way to early cancer diagnosis or monitoring progression of the cancer disease near patent bedside, homes or clinical laboratories and prevent cancer related deaths. PoC based diagnosis also offer advantageous of specificity and compatibility of using them near the patient bedside, outside fields or remote areas where resources are limited. Blood serum is the preferred source of the sample especially for performing PoC based disease diagnosis that is simple and easy to obtain.

The key factors that indicate the disease are biomarkers in serum and their levels, and PoC testings are not limited to serum sample, but also extendable to various sources, including blood, urine, saliva or sweat. Presence of a specific analyte or biomarker associated with a disease and its levels in detectable amounts enables accurate prediction and progression of a disease or contaminant or pathogen or any determinant.

The main technical problem that the proposed invention addresses are to developing a rapid, low-cost and simple immuno-optomagnetic point-of-care assay method and materials to sensitively detect and quantify target analyte, more specifically but not limited to breast cancer biomarker protein (human ErbB2/Her2 protein) from test serum samples near the patient bedside. Here, the target analyte could be any of the various other cancer or other disease biomarker proteins, bacteria, virus, nucleic acid (DNA/RNA), toxic chemicals, pesticides or drug targets.

The proposed invention, therefore, provides a rapid, low-cost and simple immuno-optomagnetic point-of-care assay method and materials that utilizes multimodal bioactive magnetic quantum dots, designed to capture analytes specifically protein biomarkers from bulk serum within 30 minutes. This invention is not limited to detection of protein biomarkers, but also used for a range of target analytes including other biomarkers, bacterial/viral infections, nucleic acids (DNA/RNA), drugs, chemicals, pesticides or environmental agents. The immuno-optomagnetic PoC biochip device and materials/components in this invention easily enables isolation or separation of target analyte with the aid of a magnet, followed by detection, upon sample application on an immuno-optomagnetic PoC biochip device.

Diagnosis signal is detected directly with a naked eye after flashing with a simple UV-torch. Accurate measurement of target analyte concentration can be made using a smartphone camera and an application to compute the RGB intensity from the immuno-optomagnetic PoC device. Corresponding to the levels of analytes present in the test sample, PoC test results are seen with a naked eye in real-time with the help of a UV-torch. In addition, advantage of RGB signal capturing using a smartphone camera and discriminating background noise and enhanced sensitivity with the method is presented in the present invention.

The advantages, including novelty/innovative aspects of proposed invention as well as superiority to prior art is summarized as follows:

i. The novelty of the proposed invention is fabrication of easy-to-use, sensitive, cost-effective and health monitoring immuno-optomagnetic nano-biosensor mediated PoC diagnostic device, assay, and method for detecting analytes in biological fluids (serum, blood, urine, saliva, sweat, CSF or interstitial fluid), water or environmental samples.

ii. The present invention describes fabrication of an easy-to-handle PoC biochip platform made of an activated glass substrate bio-functionalized with specific affinity ligands, such as antibodies. These ligands are not limited to antibodies, but can also applicable to a wide range of molecules including DNA/RNA probes, chemicals, drugs, bacteria or virus.

iii. The proposed invention involves fabrication of novel immuno-optomagnetic nanomaterials made of CdSe/CdS/ZnS quantum dot nanocrystals decorated with magnetic nanoparticles that provides unique nanoarchitecture and multimodal functionality with optical and magnetic properties combined with biological specificity to PoC device functionality.

iv. The present invention describes integration of above mentioned multifunctional MQDs with PoC device functionality for rapid, easy and accurate detection of a specific analyte, not limiting to it, but for a wide variety of target analytes including various cancers or disease biomarkers, pathogenic bacteria/virus, DNA/RNA, drugs, chemicals, or environmental agents.

v. The PoC biochip detection signal in the present invention can be obtained real-time simply by flashing a UV-LED torch and the signal is visible to a naked human eye. Such PoC functionality is currently not provided by existing methods making the developed immuno-optomagnetic PoC biochip device, assay, and method suitable for emergency situations or at remote areas where resources are limited.

vi. The fluorescence signal from the PoC biochips can either be visibly detected directly with a naked human eye, or quantified using a smartphone, equipped with a camera and a free available colorimeter application that computes RGB (red, green and blue) color intensity ratios that provides information on levels of analyte present in the test sample with reference to internal standards.

vii. The present invention related to immuno-optomagnetic PoC assay, and method does not require any laboratory equipment or trained personnel to use the device or conduct assay, unlike most existing tools and techniques used for the same purpose, including mammogram, tissue biopsy tests, ELISA tests, MRI, PET/CAT scans that makes rapid disease diagnosis extremely difficult, expensive, and time-consuming. Therefore, the novel PoC assay, materials designed, and method described in present invention provides advantages of speed, enable sensitivity, selectivity and cost-effectiveness that is lacking in current approaches, existing tools and techniques.

viii. MQDs based immuno-optomagnetic PoC in present invention provides advantages of speed, sensitivity, simplicity, portability and cost-effectiveness that is most desired in PoC diagnostic applications in resource limited settings, especially near the patient-bedsides, enabling clinicians, physicians and surgeons to take accurate clinical decisions.

In the present invention, QDs are in the center, while the magnetic nanoparticles are decorated around QDs and the MQDs particle sizes are less than 100 nm or vary between 50-100 nm providing both magnetic and fluorescent properties within the same nanocrystal making it more superior nanosized material with controllability and multi-functionality that was successfully demonstrated for its robust use in biosensing. Method employed for functionalization of MNPs present on MQDs and coupling of antibodies is easy and simple surface chemistry.

In the present invention, the QDs were intentionally designed to keep them buried in the center, while protecting them by covalently bonding with relatively smaller magnetic nanoparticles of 7-12 nm sizes on surface of QDs. Therefore, the advantage in the current invention is; (a) the MQDs sizes can be controlled from 50 nm to 100 nm useful for more sensitive and accurate biosensing that clearly distinguishes from that of the nanoparticles in prior art. (b) Also, the fact that QDs remain buried in the center while magnetic nanoparticles form a protective shell making the MQDs architecture more biocompatible. Such type of nano-configuration has not been found in the literature.

In MQDs, magnetic nanoparticles are decorated at the periphery of QDs making the MQDs to behave itself as a single bi-polar magnet, exhibiting all the features of a typical magnet at a nanoscale, while also exhibiting fluorescent properties due to embedded QDs in the core of MQDs. QDs in the center with MNPs around it prevented quenching as well as prevented from loss of optical/fluorescence signal originating from QDs. In addition, MNPs on the surface of MQDs are made available for binding site without affecting the optical/fluorescence signal from embedded QDs in the central region of MQDs.

Considering that cadmium (Cd) in CdSe/CdS/ZnS QD nanocrystals is toxic and therefore, the MQDs in present invention are intentionally designed in such a way that QDs remain buried in the center, while its direct contact with biomolecules be prevented by surface coated magnetic nanoparticles. This makes MQDs non-toxic or at least less-toxic in living beings.

In the present invention, PoC biochip platform is fabricated with a glass substrate instead of utilizing fluorescent lateral flow immunoassay because of the following reasons:

(a) PoC biochip made of glass is advantageous over LFA because, PoC biochip (glass) substrate does not require mobile phase to drive target molecule towards receptors. Whereas, LFA heavily rely on driving the target molecule by a mobile solvent for mobility or migration of target toward receptors region within LF strips. This presents major challenges in terms of impediment, non-specific adsorption of target to membranes hampering accuracy, specificity and therefore more prone to false-positive or false-negative signal. PoC based assays using glass substrates on the other hand, does not require any mobile solvent, where the sample is directly applied on glass substrate for detection, which not only saves assay time, but also prevents loss of sample or dilute target molecules.

(b) Glass substrate is inert and UV-transparent substrate more suitable for accurate measurement of fluorescence-based emissions on surfaces or through the substrates. The lateral flow immunoassays (LFA) however lack this important feature and presents disadvantages due to non-specific adsorption on membranes and impeding the binding reactions between ligand and receptor molecules.

(c) LFA based assays are not suitable for quantitative and sensitive detection of target molecules, because so far, LFA could only provide qualitative information (Yes/No). Whereas, glass based PoC biochip assays, such as that presented in our current invention has high potential and proven sensitivity, selectivity and accuracy by quantitatively detecting target molecules. The assay method presented in present invention is easy, simple, and rapid method that delivers results in 30 min.

DETAILED DESCRIPTION OF THE EMBODIMENTS

Figure 1A:
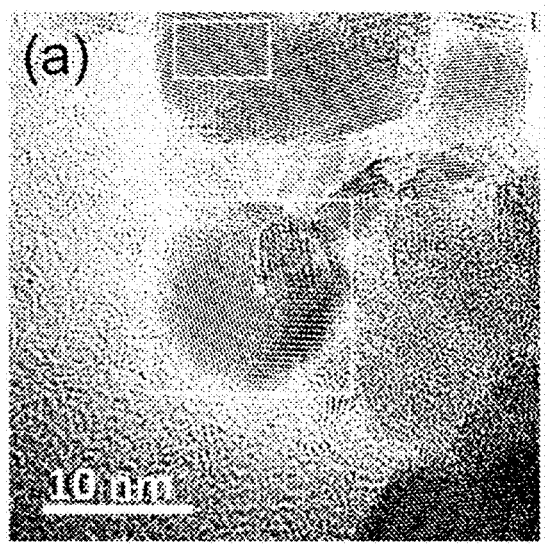
FIG. 1A shows a HR-TEM image of magnetic $Fe_3O_4$ nanoparticles (MNPs) showing size.

The present invention describes a novel immuno-optomagnetic point-of-care (PoC) assay, and method for the detection of target analyte using optomagnetic quantum dot nanoparticles (MQDs) for a rapid and sensitive PoC based cancer biomarker detection. In the present invention, a model (example) target analyte more specifically, a human ErbB2/Her2 protein, which is a breast cancer biomarker, not limiting to it but also applicable to various other cancer biomarkers was used for demonstrating PoC based detection in dilute or small sample volume of serum sample. The target analyte or sample in this invention is not limited to a specific biomarker protein or serum sample, rather it is applicable to a wide range of other analytes including various other proteins, pathogenic bacteria, virus, nucleic acids (DNA/RNA), drugs, chemicals, pesticides, or environmental agents in blood, urine, saliva, CSF, interstitial fluid, sweat or water samples.

The method used in this invention for detecting and quantifying of a target analyte in a test sample, comprising the steps of:
  i. Providing a point-of-care (PoC) glass biochip platform containing chambers functionalised with a first analyte specific reagent,
  ii. Providing multi-colored CdSe/CdS/ZnS core-shell-shell quantum dot (QD) nanocrystals made of pure single colored red and green QD nanocrystals, wherein QD nanocrystals comprise free —COOH functionality,
  iii. Providing 50-100 nm sized optomagnetic quantum dot (MQD) nanocrystals, wherein 3-10 nm sized CdSe/CdS/ZnS multi-colored QD nanocrystals are coated with 7-12 nm sized magnetic nanoparticles,
  iv. Providing a plurality of optomagnetic MQD nanocrystals functionalised with a second analyte specific reagent, capable of binding to analyte followed by the first analyte specific reagent,
  v. Contacting said MQD nanocrystals with a test sample and forming MQD nanocrystals-second analyte specific reagent-target analyte complex,
  vi. Separating said MQD nanocrystals-second analyte specific reagent-target analyte complex from test sample using an external magnet,
  vii. Loading MQD nanocrystals-second analyte specific reagent-target analyte complex in step vi. onto the PoC biochip platform in step i. and forming a sandwich complex between said PoC biochip platform and said MQD nano crystals-second analyte specific reagent-target analyte complex,
  viii. Exposing PoC biochip to UV light and detecting and/or quantifying the target analyte fluorescence signal.

Optomagnetic QD nanocrystals are bioactivated with analyte specific reagent, for example antibodies (first analyte specific reagent (Ab1) and second analyte specific reagent (Ab2)) that give rise to immuno-optomagnetic nanocrystals (MQDs-Ab2). The primary (Ab1) antibody or second (Ab2) antibody in this invention is not limited to a single protein biomarker or disease but also possibly extended to a variety of biomolecules, pathogenic bacteria, virus, DNA/RNA, environmental contaminants, pesticides or drugs which are generally described as analyte specific reagents in the present invention. In one example, human-ErbB2/Her2 biomarker protein is demonstrated but is not limited to one disease biomarker or disease condition. Both Ab2 (second antibody) and Ab1 (primary antibody) binds directly to the same analyte, but each binds from a different side (different epitope) of the same analyte. First, MQD-Ab2 binds to analyte and the exposed face of the same analyte (in MQD-Ab2-analyte complex) is presented to Ab1 on PoC biochip platform to capture. In this invention, binding of primary and second antibody to the same antigen occur at different sides or different epitopes of the same analyte.

More detailed explanation of the present invention is as follows: The immuno-optomagnetic PoC assay, or method comprises following steps;

(i) Fabrication of immuno-optomagnetic PoC biochip platform using a glass chip substrate biofunctionalized by spotting in arrays of circular spots with first receptor antibodies (Ab1) specific to a disease biomarker protein analyte, more specifically but not limited to anti-hErbB2/Her2 antibodies that specifically bind to target analyte not limiting to a specific cancer biomarker. The analyte here is not limited to a specific disease or biomarker protein, rather applicable to a range of targets, including various other cancer or other disease biomarker proteins, bacteria, virus, nucleic acid (DNA/RNA), toxic chemicals, pesticides or drug targets.

(ii) Fabrication of multi-functional optomagnetic quantum dots (MQDs) nanoprobes comprised of CdSe/CdS/ZnS decorated with paramagnetic $Fe_3O_4$ nanoparticles through a series of chemical synthesis steps described in background techniques.

Immuno-optomagnetic QD nanocyrstals (MQDs) were fabricated by;

First chemically synthesizing CdSe/CdS/ZnS QD nanocrystals followed by ligand exchange process that generated colloidal nanocrystals with free —COOH functionality designed for water solubility and PoC compatibility.

Synthesized CdSe/CdS/ZnS QD nanocrystals were chemically conjugated with as-synthesized L-aspartic acid capped MNPs (Asp-$Fe_3O_4$) to fabricate multimodal optomagnetic MQDs These optomagnetic MQDs were biofunctionalized with a second affinity ligand molecule, more specifically to a second monoclonal anti-hErbB2/Her2 antibodies (Ab2) to give rise to immuno-optomagnetic quantum dots (MQDs-Ab2).

iii) These multi-functional MQDs-Ab2 carried magnetic, optical and biological functionality that encompassed selectivity to target analyte, more specifically hErbB2/Her2 protein biomarker from dilute serum sample forming MQD nanocrystals-second analyte specific reagent-target analyte complex, more specifically MQDs-Ab2-analyte complex, magnetic property for separation/concentration and therefore served a key component in immuno-optomagnetic PoC biosensing. MQDs-Ab2-analyte complex is separated from test sample using an external magnet.

iv) MQDs-Ab2-analyte complex binds to an array of spots pre-functionalized with Ab1-on-PoC biochip platform and forms a sandwiched complex. Here Ab1 on PoC-biochip platform is designed to bind with the same analyte as Ab2 on MQDs, but with different epitope. The unique optical properties of QD nanocrystals embedded in MQDs-Ab2 provides specific, selective and sensitive optical signature that is proportional to the concentration of the target analyte present in the test sample.

v) The diagnosis signal is generated within 15-30 min of sample application and detection is made by simply flashing the surface of an immuno-optomagnetic PoC biochip with a hand-held UV-torch to illuminate MQDs.

vi) Analyte specific fluorescence response on PoC-biochips is visibly detected directly with a naked eye, as well as, quantified using a smartphone, equipped with a camera and an application for computing RGB (red, green and blue) color intensity ratios that determines the levels of cancer biomarker present in the sample.

Multimodal nature of immuno-optomagnetic MQDs-Ab2 provides magnetic, biological and optical functionality that were applied for;

(a) Selectively binding to the disease biomarker analyte present in a bulk serum (sample is not limited to any biological fluid, it can be blood, urine, sweat, CSF, interstitial fluid or water), giving rise to a MQDs-Ab2-analyte complex;

(b) Magnetically isolate/purify the MQDs-Ab2-analyte complex from the bulk serum, which is designed to concentrate the target analyte allowing resuspension in small volumes, such as a few microliters (μL), specifically 10 μL.

Figure 10:
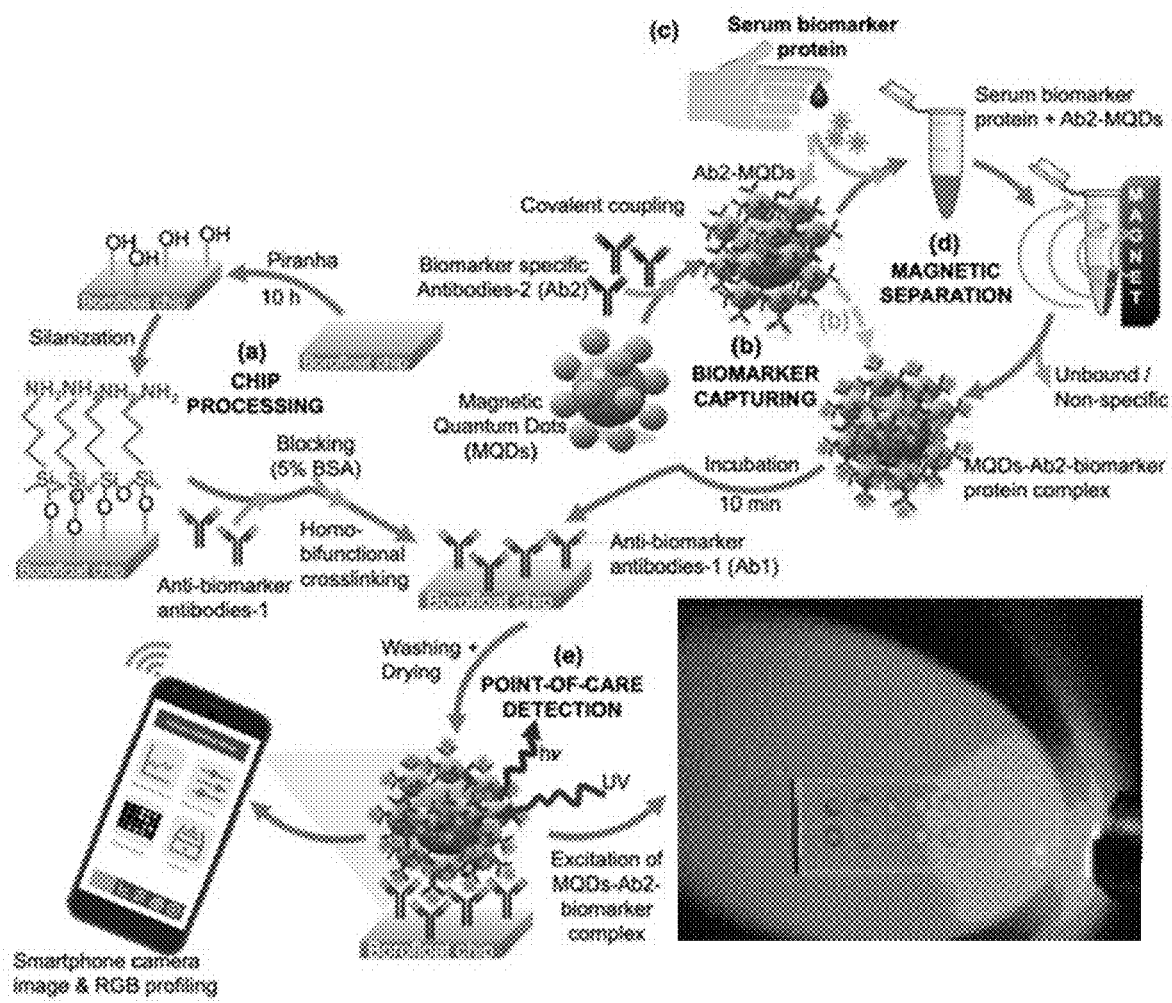
FIG. 10 shows a schematic illustration of point-of-care immuno-optomagnetic assay for detection of disease biomarker protein from a real-serum sample.

(c) Application of 5-10 μL volume of MQDs-Ab2-analyte complex suspension to sandwich on an immuno-optomagnetic PoC biochip platform with a first antibody (Ab1) spotted previously; and (d) Detection of diagnosis signal by a naked eye after simply flashing with a UV-torch that illuminate MQDs-Ab2-analyte complex on PoC biochip (FIG. 10.).

(e) The immuno-optomagnetic PoC biochip also embedded with a pair of control spots to guide any non-specific binding.

(f) A separate reference PoC biochip will be included in the assay method that will provide reference signal illuminating from known MQDs-Ab2-analyte complex on PoC biochip, which will guide the user to detect the unknown levels of target analyte.

The diagnosis signal from immuno-optomagnetic PoC device is generated within 15-30 min of sample application through the instructions described above in steps (a-f). The analyte-specific fluorescence signal from PoC device can be visualized by a naked eye or quantified using a smartphone camera with the help of a free application (colorimeter App) available in android play store for computing RGB ratios, which can be used to determine the levels of disease biomarker or analyte present in the sample, which can be a biomarker protein for different type of cancer/s or any disease, pathogenic bacteria, virus, nucleic acids (DNA/RNA), toxic chemicals, pesticides or drug targets. The developed immuno-optomagnetic PoC immunoassay method is designed for target analyte with a detection limit ranging from 620 picograms per mL to 10 nanograms per mL for disease biomarker analyte (Eg., human ErbB2/Her2 protein) which is sufficient to clinically determine the progression of a disease, such as for example cancer or disease risks with the possibility of expanding to various other antibodies or biomolecules immobilized on optomagnetic nanocrystals.

The developed immuno-optomagnetic PoC biochip response exhibited high sensitivity and specificity and greater flexibility due to multi-functionality of MQDs that rendered optical, magnetic and biological functionality.

MQDs based immuno-optomagnetic PoC method in this invention provided advantages of speed, sensitivity, simple, portability and low-cost that is most desired in PoC diagnostic applications in resource limited settings.

FIG. 10 shows detailed illustration of fabrication of immuno-optomagnetic PoC chip, MQDs bioactivation, test serum sample application and diagnosis signal detection by a naked eye.

(a) Glass chips first activated to generate free —$NH_2$ functionality with which antibodies (Ab1) for a specific disease are immobilized.

(b) The chemically synthesized immuno-optomagnetic MQDs were functionalized with second antibodies (Ab2) for the same disease biomarker protein forming MQDs-Ab2 conjugates.

(c) User directly mixes serum sample containing protein biomarker with MQDs-Ab2 conjugates that captures all the serum biomarker and forms MQDs-Ab2-biomarker complex. For small volumes, serum sample can be directly applied on chips from step (a) as highlighted by dashed arrows. Or, (d) Magnetically separate MQDs-Ab2-biomarker complex using an external magnet that not only capture serum biomarker but also allow easy and rapid concentration or separation from dilute serum.

(e) MQDs-Ab2-biomarker complex isolated from serum is loaded on to Ab1-activated biochips to capture the complex present in the sample and the biochip is exposed to a hand-held UV-torch that illuminates MQDs-Ab2-biomarker complex, and the diagnostic signal from immuno-optomagnetic PoC biochip is directly seen with a naked eye, or the fluorescence intensity from MQDs-Ab2-biomarker complex is measured quantitatively using a smartphone camera equipped with RGB profiling algorithm Further aspects and examples of the invention are described in further detail below and with reference to the accompanying examples and figures.

1. Fabrication of Point-of-Care Immuno-Optomagnetic Assay Chip Platform

Immuno-optomagnetic point-of-care (PoC) biochip platform is fabricated using a 25×73 mm UV-A transparent glass chip platform (FIG. 10, (a)). The chips were first cleaned by immersing in piranha solution for 5 h, washed the chips and then silanized by immersing in 30% APTS, (3-aminopropyl) triethoxysilane solution in acetone for 5 h under constant shaking. The chips were removed and washed thrice with acetone and dried in an oven. Grafting of free amino groups of APTS on the chip surface was confirmed by FTIR analysis. The chips were activated by incubating with 0.05% glutaraldehyde solution for 1 h and washed several times with deionized water and dried.

The activated chips were patterned with a glass marker using a mask for 2×8 array of circular chambers each with a 5 mm diameter and separated by a 5 mm distance. As a result, the chip carried 8-pairs of immuno-optomagnetic reaction spots that is sufficient to detect six pairs of varying biomarker concentrations in duplicates and one pair of spots each for negative control and blank, respectively. These circular chambers were bio-functionalized by spotting with antibodies (Ab1) specific to a disease biomarker protein, not limiting to a particular disease or antigen. In one example, a model breast cancer biomarker, human-ErbB2/Her2 protein but not limiting to it, is used but it is not limited to any disease or a biomarker. For spotting, 5 µL of 45 µg/mL antibodies (Ab1, anti-hErbB2/Her2) was incubated on each spot-on-chip at 4° C. for 4 h. The entire chip was washed with PBS, pH 7.4 and then blocked by immersing in a PBS solution containing 5% BSA protein for 1 h. The bio-functionalization of antibodies on PoC biochip platform was confirmed by FTIR analysis, as well as measuring fluorescence before and after incubation with 5 µL of 25 µg/mL FITC-labeled anti-IgG antibodies on each spot-on-chip surface.

Figure 4:
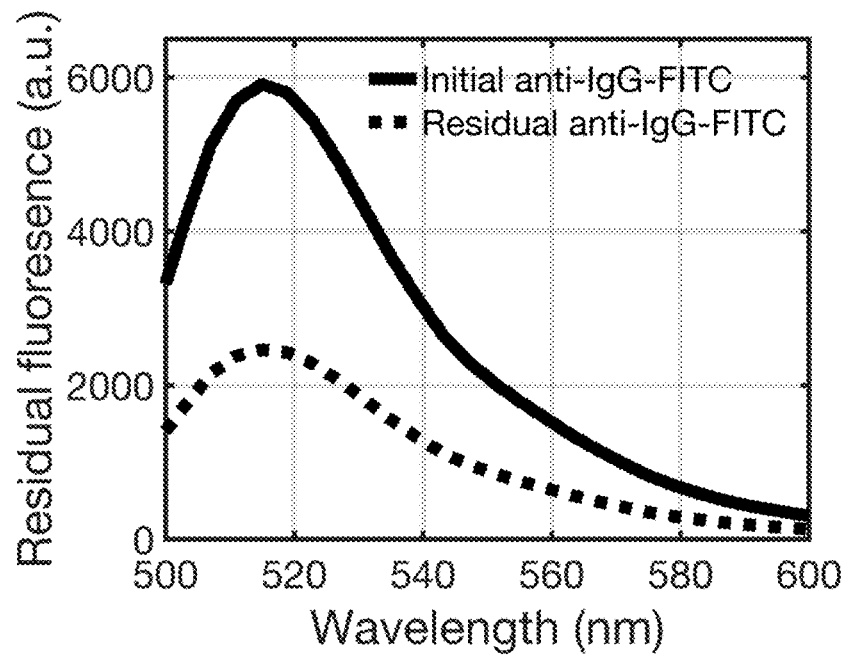
FIG. 4 shows a fluorescence spectra of residual FITC-labeled anti-IgG before and after incubation on PoC biochip platform. The arrows indicate concomitant decrease in residual fluorescence as FITC-anti-IgG binds to the Ab1 on PoC biochip platform. The inset figure shows an image of fluorescence emission from FITC-anti-IgG-Ab1 complex formed on PoC biochip platform.

The bio-functionalization of receptor antibodies on PoC biochip platform was confirmed by using anti-IgG labeled with FITC, a fluorescent dye which bind to Ab1 on PoC biochip platform. FIG. 4 shows residual fluorescence spectral peak from FITC-anti-IgG antibody measured before and after incubation on PoC biochip platform, as well as the FITC-anti-IgG-Ab1 binding was observed under the fluorescence microscope and confirmed the Ab1-on-PoC biochip platform.

2. Synthesis of Magnetic Quantum Dots (MQDs)

MQDs were synthesized by following three step reactions, These are; (A) synthesis of $Fe_3O_4$ magnetic nanoparticles (MNPs), (B) gradient synthesis of single (green/red) colored CdSe—CdS—ZnS nanocrystals, and (C) synthesis of MQDs by covalent coupling of QDs and aspartic-$Fe_3O_4$ MNPs. Details of both methods are described below:

2.1) Synthesis of $Fe_3O_4$ Magnetic Nanoparticles (MNPs)

Figure 1B:
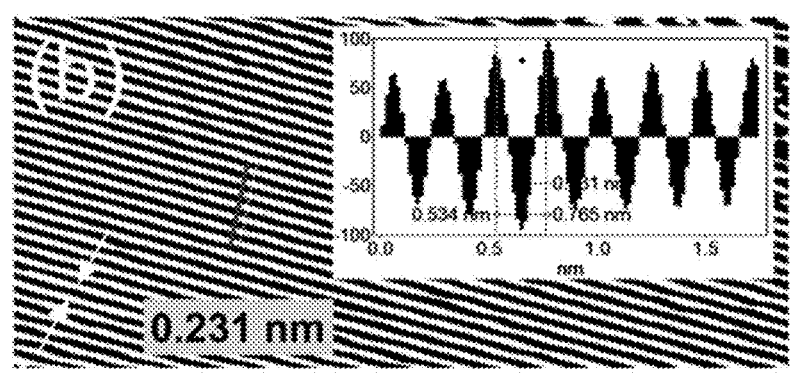
FIGS. 1B-1C show magnified section of image in FIG. 1A highlighted with rectangle and square shapes representing for lattice distance and single MNP, respectively.
Figure 1C:
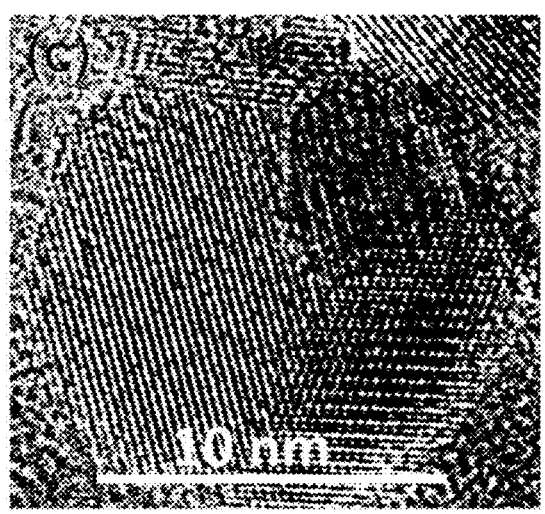

First, magnetic $Fe_3O_4$ nanoparticles were synthesized by a modified form of previously reported co-precipitation method [1]. In this method, $Fe^{+2}$ and $Fe^{+3}$ solutions were co-precipitated under alkaline conditions. For this, two separate salt solutions, such as 2 M $FeCl_2.4H_2O$ dissolved in HCl and 1.1 M $FeCl_3.6H_2O$ in deionized water were prepared. The above two solutions were thorough mixed by stirred for 15 min. In a separate container, 1 mL of above $FeCl_3.6H_2O$ and 0.25 mL of $FeCl_2.4H_2O$ were added, mixed by stirring and the solution was heated for 10 min at 80° C. Co-precipitation of $Fe^{+2}$ and $Fe^{+3}$ was initiated by dropwise addition of 3 mL of 3 M ammonia solution to the salt solution. The black precipitate of magnetic $Fe_3O_4$ nanoparticles (MNPs) were separated with the help of an external magnetic field and washed with double deionized water to remove excess chloride ions. The modified method involves the gravity separation of MNPs based on their size: MNPs suspension contained varying sizes spanning from micron-size to a few nanometers were subjected to size dependent fractionation by applying various relative centrifugal force (RCF, g). For this, gravity separation of MNPs was carried out using centrifugation at varying RCF (g) from 500-15000×g which effectively separated different nano-sized MNPs. In this invention, final smallest nanosized MNPs of 7-12 nm was obtained at 15000×g for 3 min, which were examined by HR-TEM. FIGS. 1A-1C show HR-TEM of magnetic $Fe_3O_4$ nanoparticles (MNPs) at different magnifications with clear lattice fringes that show MNPs with approx. 7-12 nm in sizes.

Figure 1D:
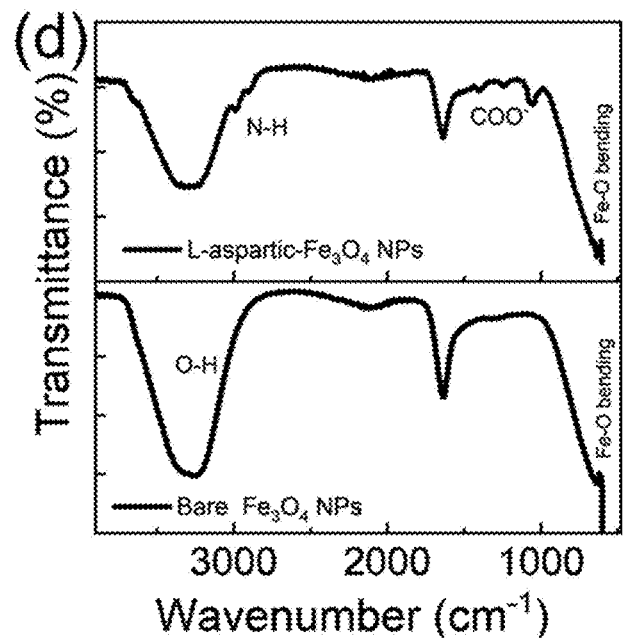
FIG. 1D shows a FTIR spectra of bare MNPs (bottom), L-aspartic acid (middle) and L-aspartic acid stabilized MNPs (top, Asp-$Fe_3O_4$ MNPs)
Figure 1E:
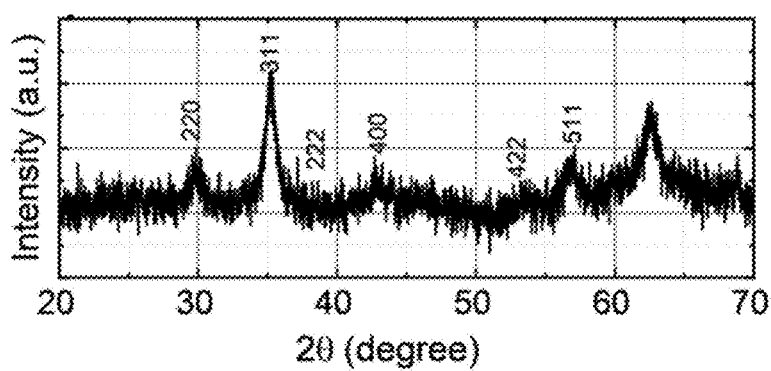
FIG. 1E shows a XRD-pattern of as-synthesized MNPs.

A final black colored MNPs fraction was subjected to stabilization as described below;

Stabilization of MNPs: Aliquots of 10 mg dry weight of bare MNPs were resuspended in 4.5 mL of freshly prepared 0.3 M ammonia solution and the suspension was dispersed by sonication using a probe ultrasonicator for 1 h. The colloidal $Fe_3O_4$ MNPs were washed in three cycles of 7 min magnetic separation using a magnetic stand followed by resuspension in 1 mL deionized water. The washed bare-$Fe_3O_4$ were dispersed in 4.5 mL of deionized water and stirred vigorously for 10 min before adding 30 mg of (S)-(+)-aminosuccinic acid (L-aspartic acid, 50 mM) and continued vigorous stirring for additional 6 h, at this stage the measured solution pH=2-3. After the reaction was completed, the pH of the solution was adjusted to 10-11 by dropwise addition of 3 M ammonia solution. Excess non-adsorbed aspartic acid was removed in successive five cycles of magnetic separation and washing with 2 mL dilute ammonia solution (0.3 M) and the aspartic acid-stabilized $Fe_3O_4$ magnetic nanoparticles (Asp-MNPs) were stored in same solution until further use for chemically coupling with nanocrystals. FIG. 1D shows FTIR spectra of MNPs before and after capping or stabilization with L-aspartic acid, confirming successful L-aspartic acid capping on MNPs (Asp-$Fe_3O_4$). FIG. 1E shows XRD-pattern of MNPs in which the peak position of all diffraction peaks of MNPs with respective plane indices (to (2 2 0), (3 1 1), (4 0 0), (4 4 2), (5 1 1) and (4 4 0)) well matched with cubic spinel phase of magnetite (JCPDS card no. 85-1436), indicating synthesized magnetic $Fe_3O_4$ NPs has crystalline magnetite phase.

2.2) Synthesis of Multi-Color Water-Soluble QD Nanocrystals 2.2.1) Gradient Synthesis of Single-Color GREEN CdSe—CdS—ZnS Nanocrystals Single color green CdSe core nanocrystals with CdS and ZnS shells were synthesized using a previously described method [2]. First, Se—S solution was prepared in a glovebox by dissolving 0.316 g selenium powder and 0.128 g sulfur powder in 3 mL TOP and placed in a desiccator under vacuum until use. In a separate three-necked flask, 0.025 g CdO, 0.87 g zinc acetate, 2.75 mL oleic acid and 10 mL octadecene were added and the flask was heated to 150° C. for 1 h under vacuum for degassing. This was followed by introducing argon gas into the flask from an inlet connected to a condenser, while vacuum tube connected at the outlet, and the reaction temperature was raised to 310° C. After stabilizing the temperature to 310° C., 1.5 mL of above Se—S solution was quickly injected to the solution while maintaining the temperature to 304° C. and waited for 20 min for reaction to complete. This procedure was optimized to obtain a single color (green) nanocrystals that were subjected to purification. The entire reaction mixture containing green nanocrystals and impurities were divided into aliquots. About 1 mL of aliquots, each diluted with 10 mL chloroform and the nanocrystals were precipitated by adding 30 mL acetone nonsolvent and centrifuged for 2 h at 4500 rpm. The supernatant was collected in a separate tube that contained residual nanocrystals for further precipitation, while the pellet was dissolved in 2 mL chloroform and precipitated again by adding 6 mL acetone and centrifuged for 2 h at same speed. This process was repeated for 10 times and the final precipitate obtained was dried at 60° C. The dried nanocrystals were subjected to ligand exchange reaction. Ligand exchange reaction is used to generate surface functionality and water solubility. The surface coating of synthesized QD nanocrystals and making the water-soluble and colloidal forms. Here, ligand exchange process was applied to transform the core-shell nanocrystal surfaces with —COOH functionality and coating outer surface of QD nanocrystals. For this, synthesized core QD nanocrystals from the above method was subjected to ligand exchange using a combination of methods described previously [3, 4]. Briefly, synthesized pure and dried core QD nanocrystals (2.85 mg) were dissolved in 1 mL chloroform. In a separate tube, 0.25 g of L-glycine was dissolved in 5 mL deionized water then 0.2 mL of carbon disulfide was added and vortexed, which yielded a polymeric milky solution. To this, entire 1 mL core QD nanocrystals (2.85 mg/mL) in chloroform was added and kept stirring for 24 h on a magnetic stirrer at room temperature. During this period, phase transfer of the QDs occurred from organic phase to aqueous phase, making the QDs more stabilized and colloidal in aqueous solution. The transfer of QDs to aqueous phase was visibly observed under the UV light. The QDs from aqueous phase was purified by diluting with deionized water in 1:4 ratio and precipitated by adding 20 volumes of acetone followed by centrifugation at 10000 rpm for 5 min for green (smaller) QDs and 30 min for red (larger) QDs, respectively. The precipitate was then re-dispersed in aqueous buffer (PBS, pH 7.4). The water-soluble core-shell QDs were later used for stabilization and capping with antibodies (Ab2), not limiting to single biomarker or BSA protein, but for a range of various other antibodies or biomolecules for analyte detection.

2.2.2) Gradient Synthesis of Single-Color RED CdSe—CdS—ZnS Nanocrystals

Red, single colored CdSe core nanocrystals with CdS and ZnS shells were synthesized as described previously [5]. Here, the Se and S solutions was prepared separately in a glovebox instead of mixing them together. For this, selenium solution was prepared by dissolving 0.158 g Se powder in 0.89 mL (0.74 g) TOP, while the sulfur solution was prepared separately by dissolving 0.192 g sulfur powder in 0.45 mL (0.37 g) TOP. These solutions were placed in a desiccator under vacuum until use. In a separate three-necked flask, 0.09 g CdO, 0.27 g zinc acetate, 3.6 mL oleic acid and 15 mL octadecene was poured and degassed by heating at 150° C. for 1 h under vacuum. The argon flow at the condenser inlet was turned on and raised the reaction temperature in flask to 300° C. Once the temperature was stabilized, 0.1 g of Se solution was quickly injected to the reaction mixture using a syringe needle, after 90 seconds, 0.018 mL dodecanethiol was added gradually by slow injection and the reaction was allowed to continue for 15 min. Lastly, 0.29 g sulfur solution prepared previously was injected into the reaction flask and waited 15 min for reaction to complete and removed the flask for cooling the reaction mixture. About 15 mL of the reaction mixture containing red CdSe/CdS/ZnS nanocrystals was diluted with equal volume of chloroform and precipitated by adding 45 mL acetone and centrifuged for 15 min at 4500 rpm. The supernatant was removed, and the pellet was re-dissolved in 2 mL chloroform and re-precipitated by adding 6 mL acetone, centrifuged for 5 min at 4500 rpm and the process was repeated at least 8 times. Finally, the precipitate was dried at 60° C. overnight and the dried powder yielded 73 mg of CdSe/CdS/ZnS nanocrystals that was subjected to ligand exchange as described above.

2.2.3) Bright Yellow Colored CdSe—CdS—ZnS Nanocrystals

Figure 2:
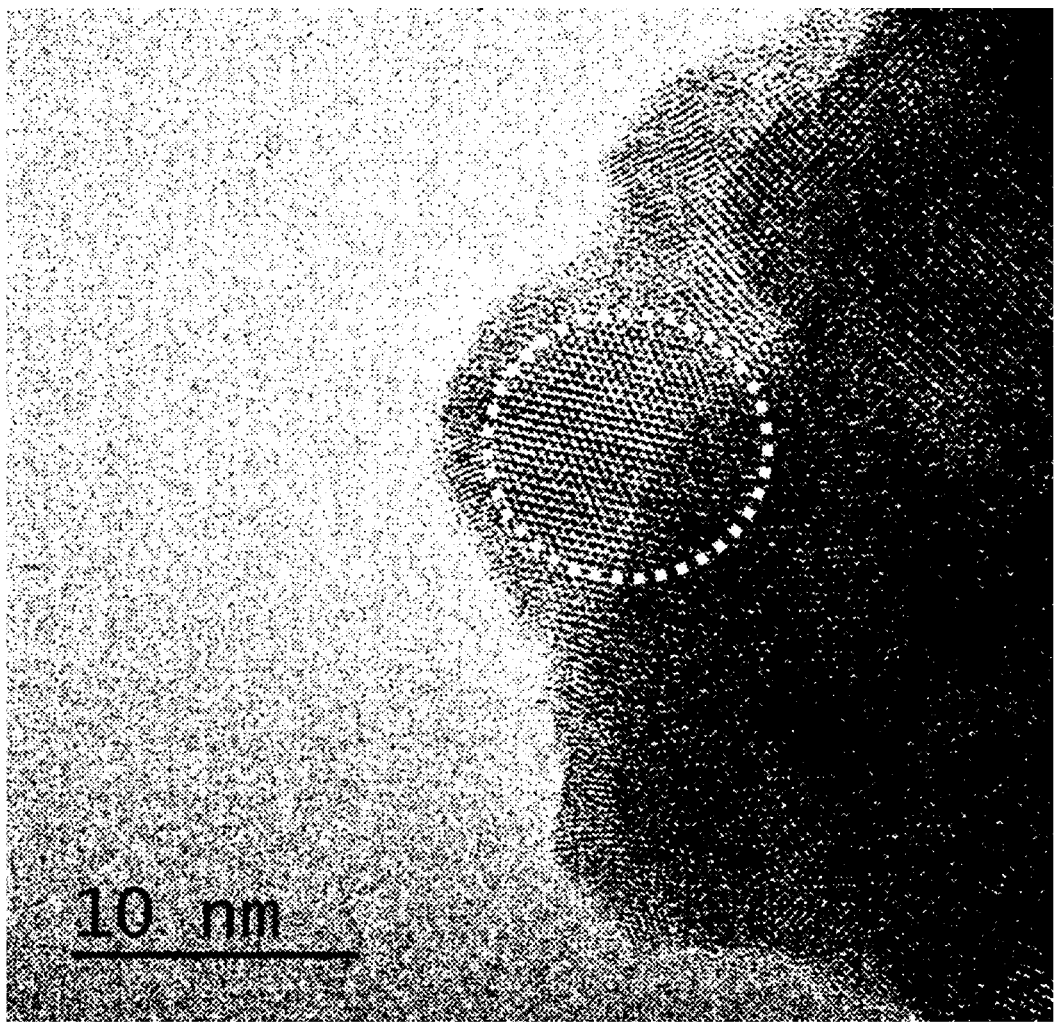
FIG. 2 shows a HR-TEM image of chemically synthesized CdSe/Cds/ZnS core-shell-shell quantum dot nanocrystals following ligand exchange with free —COOH functionality. The dotted circle represents a single CdSe/Cds/ZnS core-shell-shell nanocrystal whose outside surface is coated with a thin hydrophilic layer of dithiocarbamate chains with free —COOH functionality.

The above synthesized pure single colored Red and Green QD nanocrystals were mixed in 1:1 ratio that yielded yellowish/orange colored colloidal suspension that had emission at ~585 nm. These crystals were employed for immuno-optomagnetic PoC biochip assays. CdSe/CdS/ZnS core-shell-shell QD nanocrystals were separately synthesized using a combination of methods and ligand exchange process and surface functionality as described in background methods. FIG. 2 shows HR-TEM image of a representative CdSe/CdS/ZnS core-shell QD nanocrystals showing core-shell nanostructure with a clear 3-10 nm sizes.

Figure 3A:
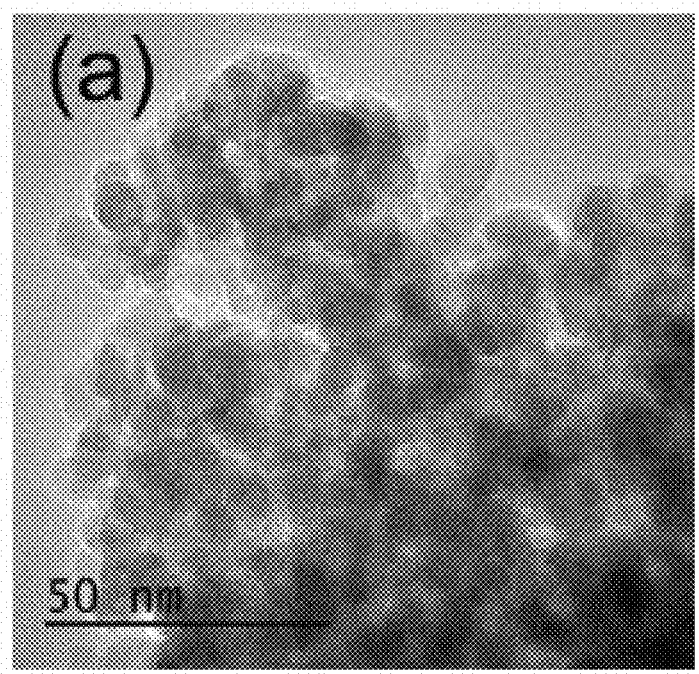
FIGS. 3A-3B show HR-TEM images of MQDs at different magnifications.
Figure 3B:
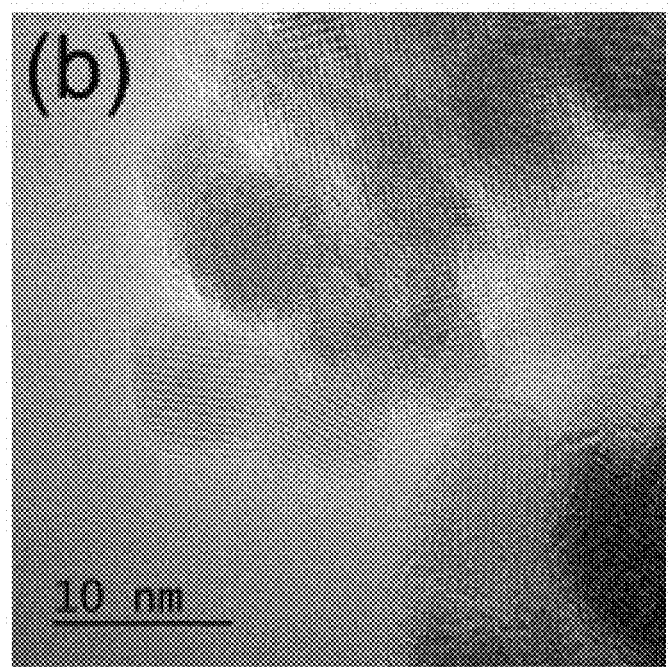
Figure 3C:
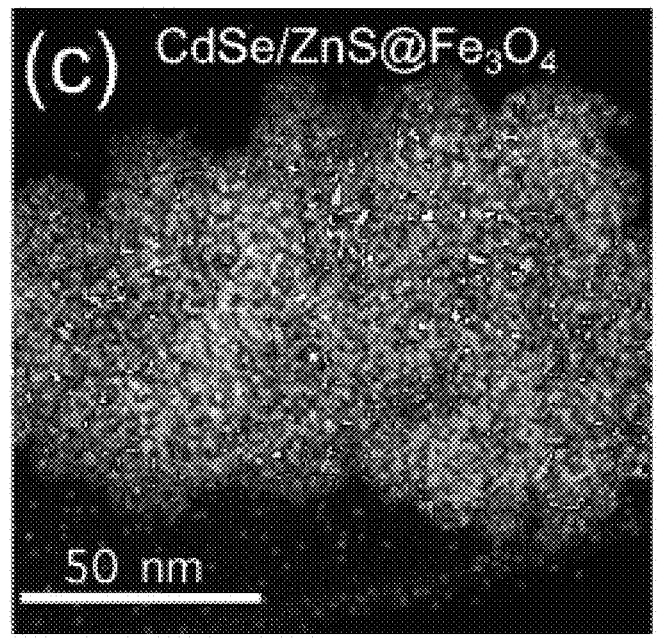
FIG. 3C shows an overlaid EDS map of MQDs showing different colors representing different elements of MQDs.
Figure 3D:
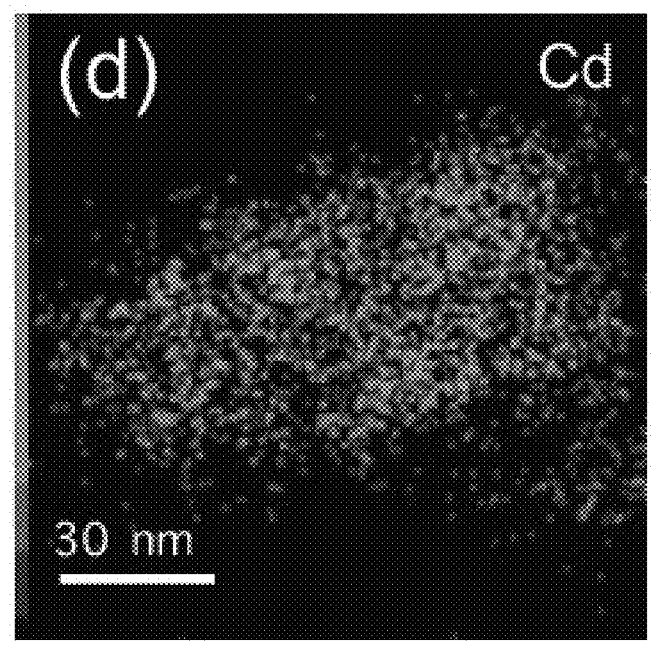
FIGS. 3D-3F show individual maps for Cd, Fe and S elements, respectively derived from MQDs. The red and orange colors representing Cd and S elements, respectively were found surrounded by Fe elements forming MQDs.
Figure 3E:
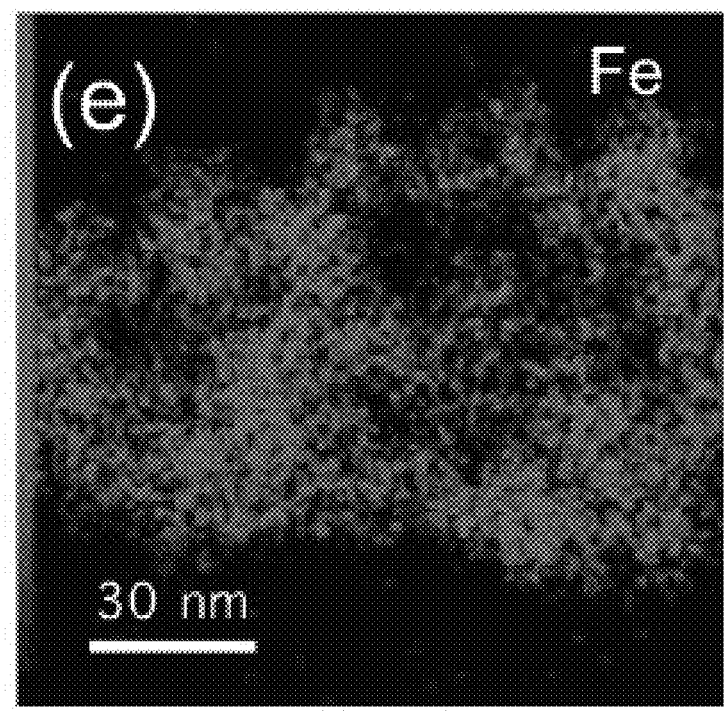
Figure 3F:
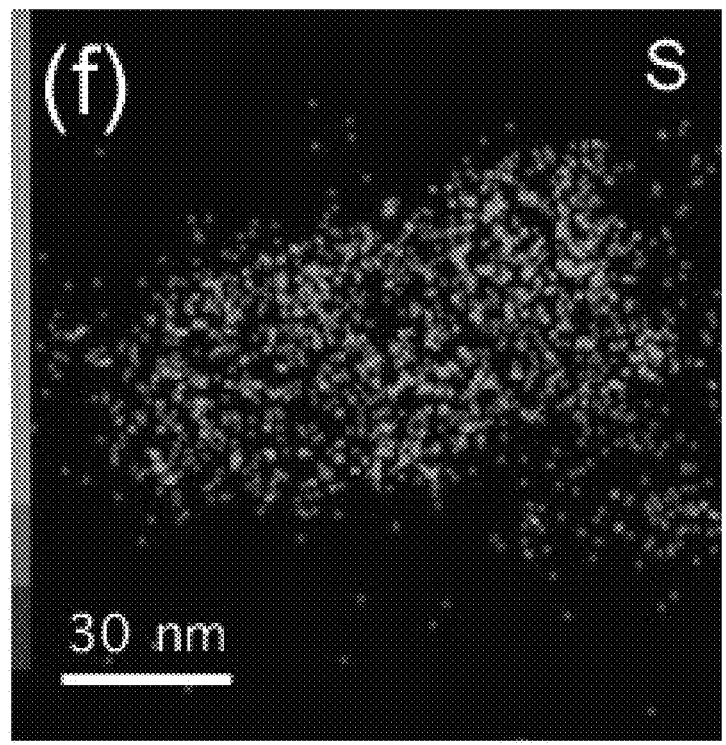
Figure 3G:
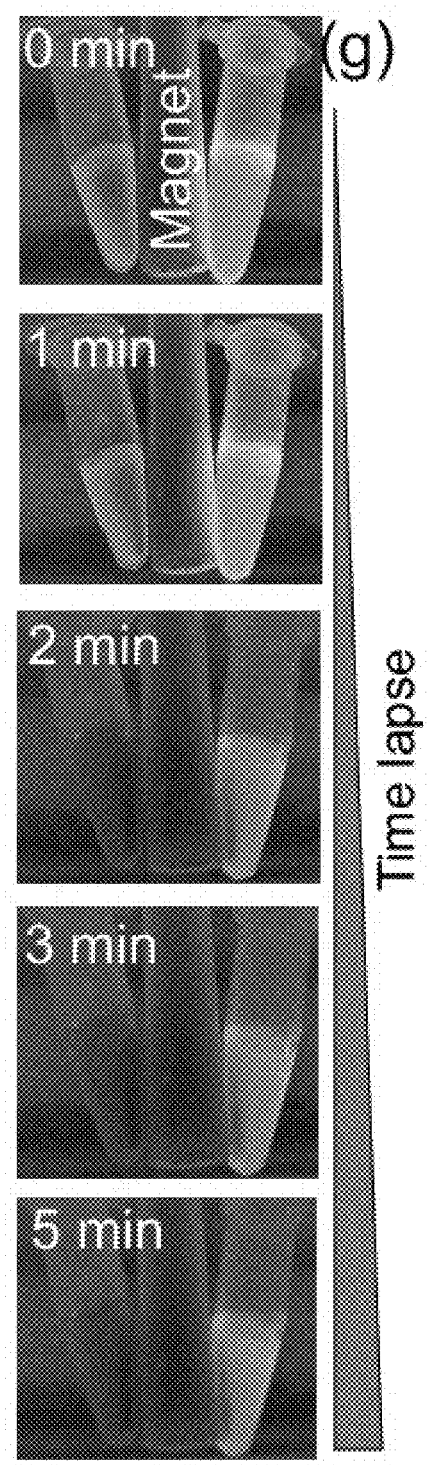
FIG. 3G shows time-lapse images taken during the magnetic separation process using a magnet from 0-5 min with two different colloidal magnetic quantum dots (MQDs) with emissions at 525 nm and 585 nm, respectively.

2.2.4) Chemical Assay to Demonstrate Separation of Magnetic and Non-Magnetic Nanocrystals Chemically synthesized multi-color QD nanocrystals generated during different time intervals were collected separately. The red and green nanocrystals having emissions at 655 and 545 nm, respectively were taken and chemically coated with magnetic $Fe_3O_4$ nanoparticles. The green and red nanocrystals were mixed in an equimolar ratio with respect to their emission fluorescence intensities that gave rise to a third bright color yellowish orange color, which was conjugated with MNPs for immuno-optomagnetic PoC detection application. FIG. 3G shows time-lapse of magnetic separation of green and bright orange MQDs within 5 min. This result is a clear evidence that optomagnetic MQD nanocrystals are unique multi-modal nanomaterials that are not limited to specific application, but also applicable to clinical diagnosis, monitoring drugs, detecting pathogenic bacteria/virus, nucleic acids (DNA/RNA), chemicals and environmental toxicants making them versatile tools for detection.

2.3) Synthesis and Characterization of Optomagnetic Quantum Dot (MQD) Nanocrystals Magnetic quantum dots (MQDs) were synthesized using CdSe/Cds/ZnS core-shell-shell QD nanocrystals and MNPs by systematic sequential chemical conjugation process that gave rise to specific orientation in which central QD nanocrystals were decorated on its surface with MNPs as described in background methods.

The stabilized water-soluble, core-shell-shell CdSe/CdS/ZnS QD nanocrystals (0.28 mg) with free carboxyl functionality were dispersed in 0.5 mL deionized water and dispersed by sonication for 5 min using a mini-probe ultrasonicator (Sonopuls mini20). To this, 100 µL of freshly prepared 150 mM of 1-ethyl-3-(3-dimethylaminopropyl) carbodiimide hydrochloride (EDC) was added and incubated for 5 min and then added 100 µL of 300 mM N-hydroxysuccinimide (NHS). The above reaction mixture was incubated for 5 min and the EDC-activated bright fluorescent nanocrystals were mixed with 1 mL of 10 mg/mL of Asp-MNPs (7-12 nm) suspension. The mixture was incubated for 2 h at room temperature for covalent coupling under vigorous shaking. The resulting reaction mixture contained hybrid CdSe/CdS/ZnS@MNPs nanoparticles (magnetic quantum dots, MQDs) were magnetically separated and washed by resuspending in PBS solution, pH 7.4.

Synthesized QDs and MQDs were characterized with respect to composition and morphology/size by X-ray-diffraction (XRD) and Transmission Electron Microscopy (TEM) and elemental analysis using energy dispersive X-ray (EDX) mapping, respectively.

Coating of MNPs on QD-nanocrystal surfaces was confirmed by EDX analysis, as well as after magnetically separating MQDs followed by direct UV irradiation at 365 nm, which accompanied by disappearance of fluorescence from the supernatant solution. FIGS. 3A-3F show HR-TEM images and EDS maps of elements in MQDs. Identified elements from EDS of MQDs revealed percentage of each element, such as Cd (15%), Se (3.8%), Zn (6.7%), S (21%), Fe (22%) and O (21%), respectively.

The representative EDX maps shown in FIGS. 3A-3F confirmed that the QD nanocrystals were surrounded by magnetic $Fe_3O_4$ nanoparticles forming MQD nanocrystals architecture that varied in sizes from 50-100 nm aggregates, each composed of 7-12 nm magnetic $Fe_3O_4$ nanoparticles surrounding the core/central 3-10 nm CdSe/CdS/ZnS nanocrystals that can be magnetically separated (FIGS. 3C-3F).

FIG. 3G shows time-lapse images demonstrating magnetic separation of synthesized two different colored model MQDs within 5 min. The synthesized optomagnetic MQDs were employed for immuno-optomagnetic PoC detection of breast cancer biomarker in serum that can also be applicable to various other cancer types, different diseases, DNA/RNA, viruses or bacteria, pesticides, chemicals, environmental agents and others.

3. Biofunctionalization of MQDs with Monoclonal Antibodies (Ab2)

As-synthesized MQDs (10 mg) were suspended in 500 µL of PBS solution and homogeneously dispersed using miniprobe ultrasonicator for 5 min and then activated by adding 100 µL of 100 mM EDC and 150 mM NHS and incubated for 5 min. The activated MQDs were separated using a magnetic stand and washed with PBS solution and the process was repeated three times. The resulting suspension was divided into several aliquots and each were covalently coupled by incubating with 100 µL of 45 µg/mL second antibody (Ab2) specific to disease biomarker protein similar to Ab1 (eg., anti-ErbB2/Her2 antibodies), or BSA protein (negative control), or anti-FGF or anti-VEGF antibodies (negative controls), respectively for 4 h at 4° C. under constant shaking for covalent coupling. The Ab1 or Ab2 in this invention is not limited to single protein biomarker or disease but also possibly extended to a variety of biomolecules, pathogenic bacteria, virus, DNA/RNA, environmental contaminants, pesticides or drugs.

The MQDs synthesized chemically were designed to carry free —COOH functionality in order to easily functionalize by covalent conjugation of a second antibody (Ab2) for the same target analyte that Ab1 binds. In this invention, like Ab1, Ab2 is also not limiting to a specific target analyte, rather it is applicable to range of other target analytes, including various other cancer biomarkers or disease protein biomarkers, pathogenic bacteria or virus, nucleic acids (DNA/RNA), pesticides, chemicals, environmental agents and others. In this invention, second anti-hErbB2/Her2 (Ab2) monoclonal antibodies are used to generate Immuno-optomagnetic nanocrystals (MQDs-Ab2).

Figure 5:
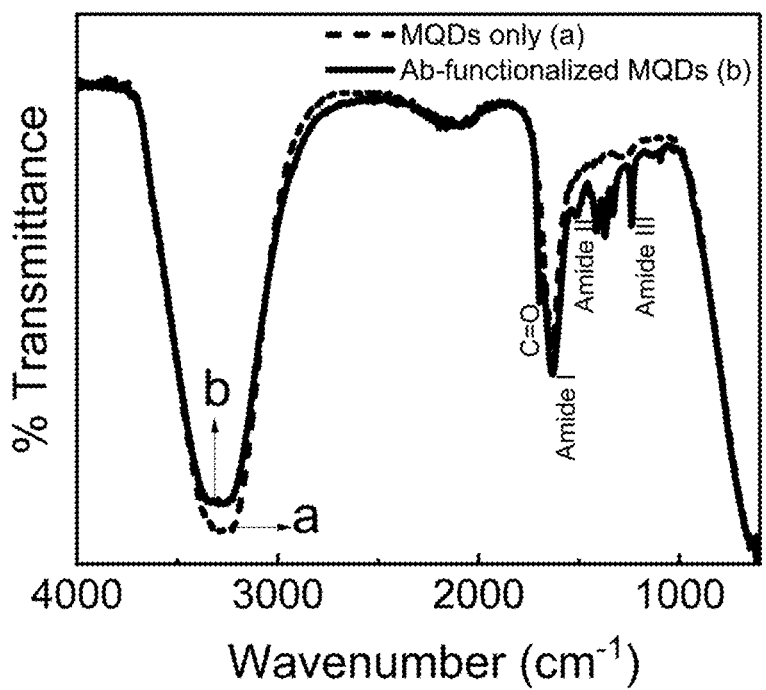
FIG. 5 shows a FTIR spectra of (a) MQDs and (b) Ab2-immobilized MQDs.

The immobilization of Ab2 on surface activated MQDs was confirmed by FTIR analysis. MQDs-Ab2 were confirmed by FTIR analysis and FIG. 5 shows FTIR spectra of MQDs before and after Ab2 immobilization. Ab2 functionalized MQDs exhibited presence of amide III related to C—N stretching and N—H bending near a wide region of 1200-1350 $cm^{-1}$, which is a complex amide band and strongly depends on the number of side chain and nature of hydrogen bonding. The peaks at 1632 and 1511 $cm^{-1}$ corresponds to antibody (Ab2) functionalization related to amide I and amide II group linkage on MQDs. The peak at 1717 $cm^{-1}$ was related to C=O of amino acid. The above result clearly confirmed successful Ab2 bio-conjugation on MQDs.

These multi-functional MQDs-Ab2 carried biological, optical and magnetic properties that capture analyte, illuminate upon excitation and magnetically separate, respectively due to which they were employed for PoC based detection, which is not limited to any specific disease detection, but also for various other analyte targets, including various cancer biomarkers, pathogenic bacteria or virus, nucleic acids (DNA/RNA), pesticides, chemicals, drugs or environmental agents.

4. Immuno-Optomagnetic PoC Testing Method and Components

Immuno-optomagnetic PoC tests were carried out using model serum samples spiked with known biomarker protein concentrations (human-ErbB2/Her2 biomarker protein) is demonstrated but is not limited to one disease biomarker or disease condition. Immunomagnetic PoC tests was performed by following steps: At the beginning, test analyte sample requires 1:1 dilution using a diluent solution (PBS, pH 7.4) to allow PoC tests to cover low-to-high risk levels of analyte.

In this invention, in one example, a case scenario of breast cancer diagnosis using hErbB2/Her2 biomarker protein, not limiting to it but also applicable to various other cancer biomarkers is demonstrated using reported levels for normal (2-15 ng mL$^{-1}$) and high risk (15-75 ng mL$^{-1}$) levels in serum, respectively [6-8].

(a) First, the user adds immuno-optomagnetic nanocrystals (MQD-Ab2) with a few mL of test sample, which could be any biological fluid including serum, blood, CSF, urine, interstitial fluid or sweat as described in background method. Preferably in this invention, the user adds 1 mg of immuno-optomagnetic nanocrystals (MQD-Ab2) with a few drops of pre-diluted serum sample spiked with a known concentration of protein biomarker, not limiting to specific disease were used and mixed for 5 min.

b) After this process, with the aid of MQD-Ab2, which is designed to capture dilute analyte (biomarker protein) from serum or any biological fluid or solvent, which gives rise to an immuno-optomagnetic QD nanocrystals-analyte; MQD nanocrystals-second analyte specific reagent-target analyte complex, more specifically MQDs-Ab2-analyte complex (MQDs-Ab2-hErbB2) complex.

c) The sample is placed on a magnet/magnetic stand and the complex of MQD-Ab2-biomarker protein formed is magnetically separated.

d) The concentrated MQD-Ab2-hErbB2 complex is dispersed ~10 μL volume capacity with supplied diluent, here it is phosphate buffered saline (PBS, pH 7.4), which is then dropped to sandwich with Ab1 spot present on a PoC biochip platform.

e) The PoC-biochip platform pre-functionalized with Ab1 (in this invention, primary anti-hErbB2 antibodies), which bind specifically with MQD-Ab2-hErbB2 complex on chip within 10 min at 37° C. After this, the user drains the residual or unreacted molecules by blowing with an airbulb and washed three times with diluent solution (PBS) and dried.

f) User then flashes a hand-held UV-torch on PoC biochip surface, and the signal is generated upon illuminating MQDAb2-biomarker-Ab1-complex-on-chip that is visibly detected. This signal will be directly proportional to biomarker level in a defined volume of serum.

g) User will quantify the levels of biomarker present in the serum sample simply by capturing image and using a smartphone equipped with camera and a colorimeter App in android operating system. The signal generated from the PoC-biochip platform is proportional to the analyte concentration present in the test sample. In this invention, model biomarker concentration is tested, where the intensity of fluorescence emission from MQD-Ab2-hErbB2 complex-on-chip provided an accurate quantitative estimation of analyte hErbB2/Her2 cancer biomarker levels present in the test serum, which was measured using a smartphone equipped with camera and a colorimeter App with image processing and RGB-computing algorithm in android operating system. The analyte here is not limited to breast cancer related hErbB2 biomarker, but also applicable to various other types of cancer biomarkers, nucleic acids, bacteria, virus, pesticides, chemicals, environmental agents and others 5. Smartphone Assisted PoC Signal Detection In this invention, following results of model analyte (hErbB2/Her2 protein biomarker) detection is presented, which is not limited to specific disease biomarker protein, but for a wide variety of target analytes including various other cancer or disease protein biomarkers, pathogenic bacteria or virus, nucleic acids (DNA/RNA), pesticides, chemicals, drugs, or environmental agents.

FIGS. 6A-6G show signal generated from immuno-optomagnetic PoC chip is recorded using a smartphone camera and a colorimeter App equipped with image processing and RGB-computing algorithms in android operating system.

Figure 6A:
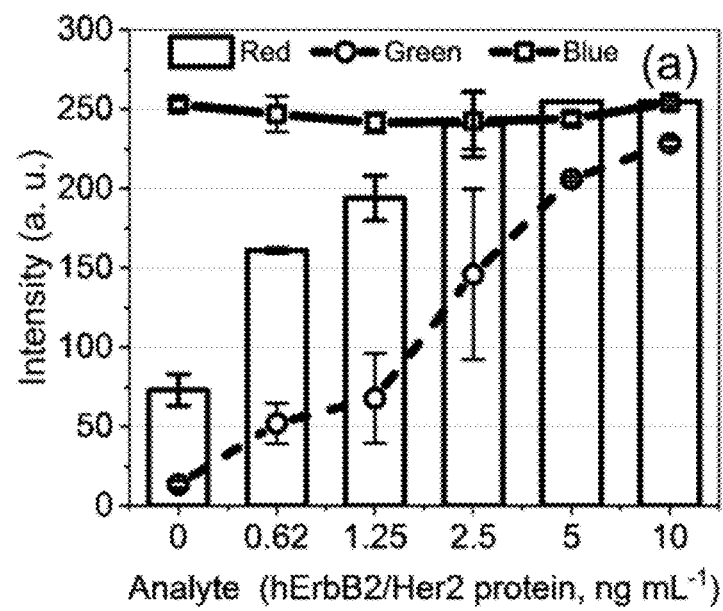
FIG. 6A shows red, green and blue (RGB) intensities against varying analyte concentrations (eg., hErbB2/Her2 biomarker) derived from 8 bit RGB images of UV-illuminated point-of-care immunoassay chips taken by a smartphone camera equipped with RGB-computing algorithm in an android operating system. The algorithm computed RGB intensities in replicate measurements (n=2 to 5) corresponding to varying analyte concentrations (0-20 ng mL$^{-1}$ serum hErbB2/Her2) form point-of-care immunoassay chip.
Figure 6B:
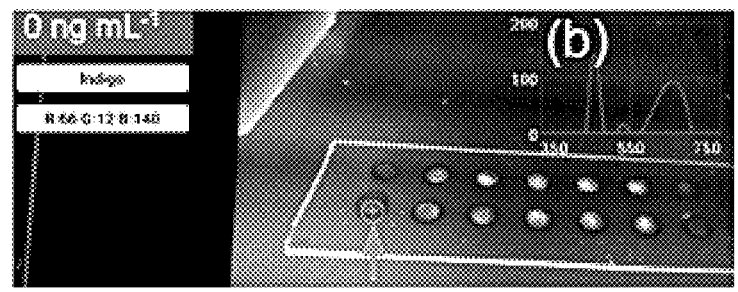
FIGS. 6B-6G show screenshot images of a smartphone during the alignment of cursor/pointer on each spot-on-PoC-biochip surface (highlighted by arrows) that displayed respective RGB values (shown in the insets) in relation to an analyte concentrations present in the test sample, respectively. The insets in FIGS. 6B-6G also show a spectra of intensities against the function of wavelengths which is a part of display output in smartphone App (colorimeter).
Figure 6C:
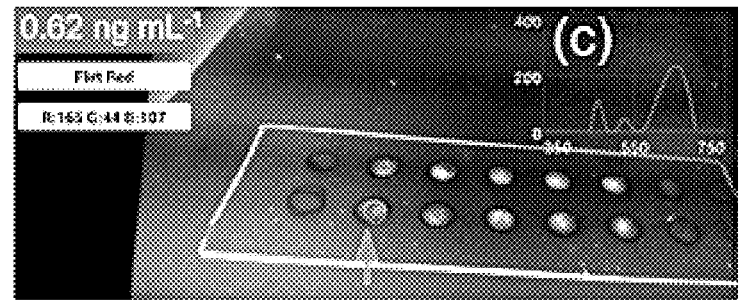
Figure 6D:
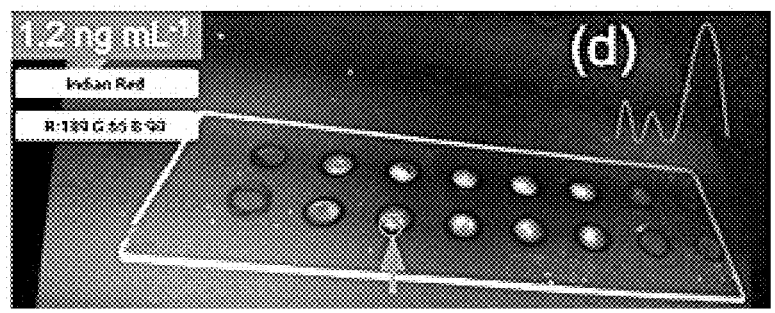
Figure 6E:
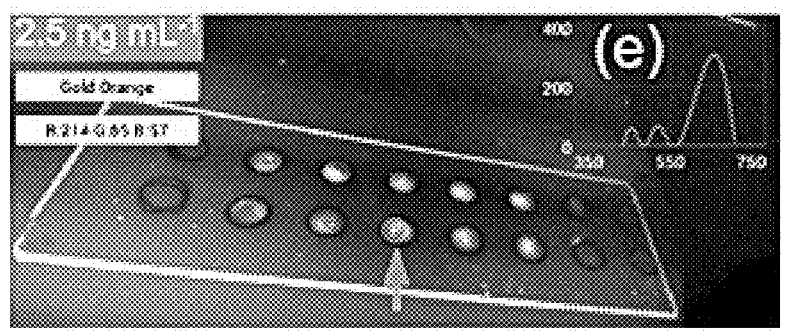
Figure 6F:
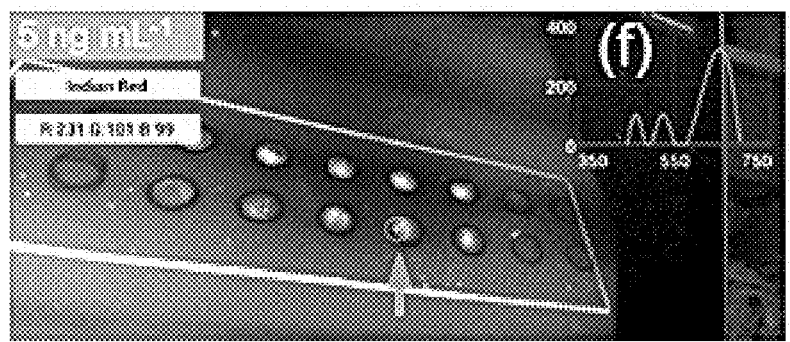
Figure 6G:
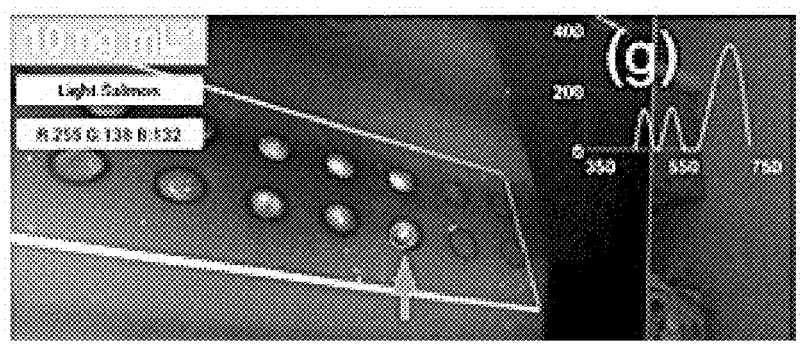

The smartphone first captures the image of PoC-biochip platform while it is illuminated by a hand-held UV-torch as illustrated in FIG. 10. The captured image is then processed by the colorimeter application pre-installed in the same smartphone, which computes the fluorescence intensity signal and calculates biomarker concentration with respect to standard controls. FIGS. 6A-6G show results of example analyte detected from intensity values from red, green and blue channels. The intensity profiles of red, green and blue (RGB) channels derived from 8 bit RGB images are shown in FIG. 6A. The algorithm computes RGB intensity values corresponding to varying analyte concentrations (in this invention, for example 0-20 ng mL$^{-1}$ serum hErbB2/Her2) form immuno-optomagnetic PoC biochip.

The 8-bit ($2^8$=256) different RGB levels provides greater precision and computed small changes in PoC-biochip response colors especially originating from the fluorescence emission by MQDs-Ab2-analyte-Ab1-on-chip, which is directly proportional to the analyte (here, cancer biomarker) levels in test serum sample. Further, detection of analyte (eg., serum hErbB2/Her2) levels was made possible within 15-30 min of sample loading.

The method demonstrated in this invention required no additional steps or reagents, making the present invention related to immuno-optomagnetic PoC biochip platform most desirable for not limiting to clinical diagnosis but also applicable for a whole range of other areas, such as detection of other cancer types, pathogenic bacteria, virus, nucleic acids (DNA/RNA), pesticides, chemicals, drugs or environmental agents.

FIGS. 6B-6G show representative screenshot images of a smartphone application taken after a simple alignment of cursor/pointer on each spot-on-PoC-biochip platform (highlighted by arrows) that displayed respective RGB values in relation to specific analyte concentrations (eg., hErbB2/Her2 protein biomarker, but not limited to it) present in the test serum sample. The color variants with respect to biomarker levels are shown embedded in respective images as a part of smartphone application display output (FIGS. 6B-6G). Only red (R) and green (G) channels are responsive to immuno-optomagnetic MQD-Ab2-analyte complex on PoC biochip platform that displayed concentration dependent increasing intensity values until reaching to a saturation point at 10 ng mL$^{-1}$ of analyte (hErbB2/Her2 protein, but not limited to it) against the blue (B) background. The blue (B) channel however, designed to remain unaffected during the entire immunoassay process and therefore it is used to determine background noise or control.

The present invention demonstrates immuno-optomagnetic PoC-test performance using a model analyte (hErbB2/Her2 biomarker protein), which is relevant to breast cancer diagnosis and not limiting to it but also applicable to various other cancers or disease biomarker proteins, nucleic acids, bacteria, virus, pesticides, chemicals, environmental agents and others. The above said example of PoC tests that is designed to sense normal individuals' levels of hErbB2/Her2 protein between 2-15 ng mL$^{-1}$, while its high-risk levels reported to be 15-75 ng mL$^{-1}$ present in breast cancer patients' blood samples [6-8].

In the present invention, the maximum limit of detection (LOD) was intentionally optimized to 10 ng/mL$^{-1}$ biomarker protein analyte, which falls within the borderline reported levels for hErbB2/Her2 protein concentrations in healthy individuals [6-8], and therefore, any further increased levels of analyte in the test sample necessitates dilution for detection for high risk individuals. Dilution of test sample analyte is set as a prerequisite step at the beginning of the PoC tests as described in the background method.

6. Validation of Immuno-Optomagnetic PoC Detection by Conventional Signal Image Processing 6.1) Validation of Immuno-Optomagnetic PoC Detection by Indirect Method Immuno-optomagnetic PoC biochip functionality was validated by a conventional image processing free available ImageJ software. First, a photographic image of the UV-illuminated PoC biochip post-immuno-optomagnetic reaction was captured by a smartphone camera. The fluorescence emission signal intensity from the image proportional to biomarker concentrations (MQD-Ab2-biomarker-Ab1 complex) were calculated by ImageJ software. Pixel intensities from the UV exposed chips were plotted against the concentration and the results were compared with those obtained using smartphone camera and a colorimeter App as described above.

Figure 7:
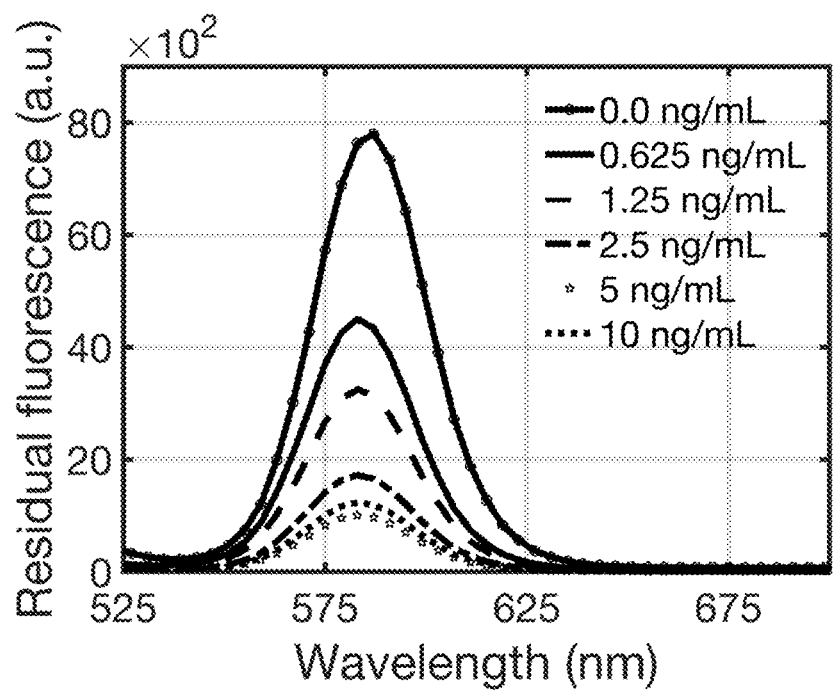
FIG. 7 shows residual fluorescence intensity measured from the unreacted and free MQD-Ab2 isolated post-incubation on immuno-optomagnetic PoC biochip-surface. The fluorescence intensity declines with respect to varying concentrations corresponded well with increasing signal from increasing analyte (serum hErbB2/Her2) levels or MQD-Ab2-analyte complex formed on the PoC biochip platform. The data shown in plot are derived from independent replicate experiments (n=3).

After application of test analyte sample and incubation on PoC biochip platform, the residual unreacted MQD-Ab2 sample on chip provides an indirect measurement of the analyte concentration, which is used to match with PoC test signal or detected immuno-optomagnetic PoC biochip signal. FIG. 7 shows the residual fluorescence from unreacted MQD-Ab2 demonstrating that stoichiometric binding of MQD-Ab2-hErbB2 complex occurred on PoC biochip platform. The concentration dependent declining residual fluorescence intensities from unreacted MQD-Ab2 was consistent with increasing signal observed with immuno-optomagnetic MQD-Ab2-hErbB2 complex measured from PoC biochip platform as observed in above FIG. 6A.

The trends from the above estimations was found directly proportional to the levels of target analyte (hErbB2/Her2 biomarker) present in the test serum sample. Here, the target analyte or the analyte sample is not limited to biomarker protein or serum, respectively, rather it is applicable to whole range of target analyte or sample solution, such as other cancers or disease biomarkers, bacteria, virus, nucleic acids (DNA/RNA), drugs, chemicals, pesticides, or environmental agents.

6.2) Validation of Immuno-Optomagnetic PoC Detection by Conventional Signal Image Processing Method Results of immuno-optomagnetic PoC biochip functionality was validated by a conventional image processing software (ImageJ) that demonstrated successful detection of analyte (human ErbB2/Her2) in serum using immuno-optomagnetic PoC biochip with a limit-of-detection of 0.62-10 ng mL$^{-1}$ hErbB2/Her2 biomarker protein in serum.

Figure 8A:
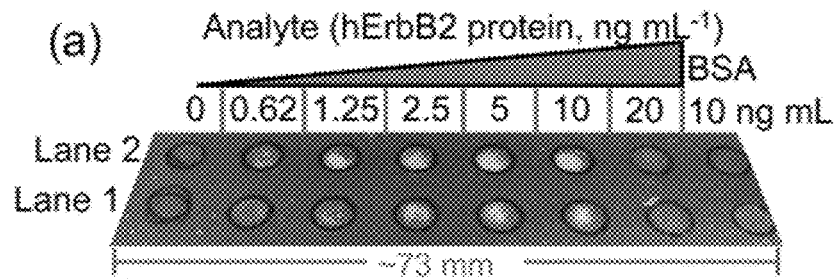
FIG. 8A shows a real image of immuno-optomagnetic point-of-care (PoC) biochip exposed to UV light (365 nm) taken by a smartphone camera showing fluorescence emission signals from MQD-Ab2-analyte complex that was captured by Ab1 present on PoC biochip. The concentration dependent increase in fluorescence intensity corresponded to the increasing levels of analyte (hErbB2/Her2) present in serum until saturation at a 10 ng mL$^{-1}$ level.
Figure 8B:
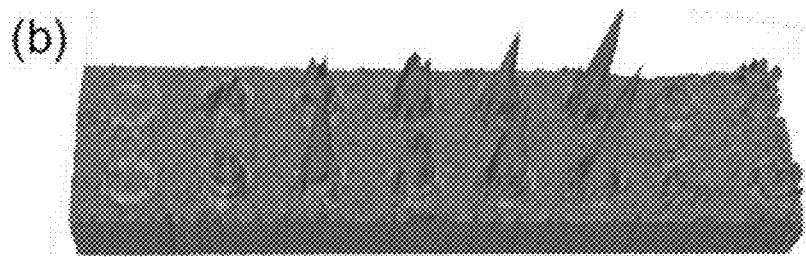
FIG. 8B shows a 3D profile of signals observed on biochip in FIG. 8A.
Figure 8C:
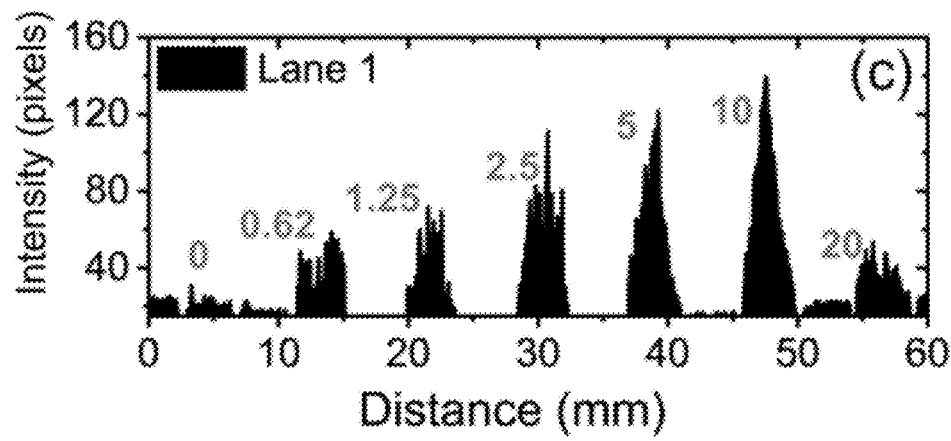
FIGS. 8C-8D show maps of areas-under-the plot generated using fluorescence intensities from Lanes 1 and 2 in FIG. 8A, respectively. Values of these areas-under-the-plot were calculated as pixel intensities using an image processing software (ImageJ) that were plotted as a function of distance (mm) separated on biochip.
Figure 8D:
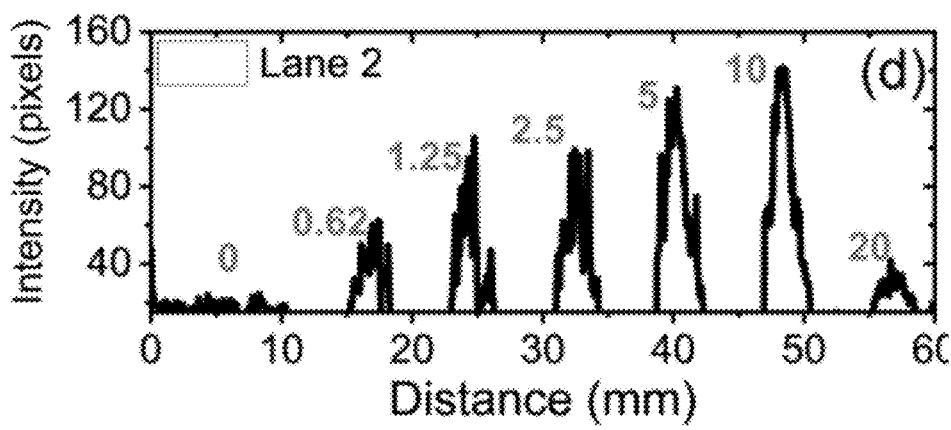

FIG. 8A shows an image of UV-illuminated immuno-optomagnetic PoC biochip captured post-immunoreaction by a smartphone camera. The fluorescence emissions from MQD-Ab2-analyte complex and their signal intensities proportional to varying analyte levels were calculated using Image J software. The results demonstrated that the diagnostic signal from developed immuno-optomagnetic PoC biochip was visible to naked-eye and that it was possible to distinguish concentration-dependent linear increase in fluorescence intensities (FIGS. 8A-8B). Quantified pixel intensities from the UV-exposed chips was consistent to visible inspection made, as well as that by using a simple smartphone camera and a colorimeter App described above (FIGS. 6A-6G and 8C-8D).

7. Specificity of Immuno-Optomagnetic PoC Tests

Specificity tests of the developed immuno-optomagnetic PoC test was carried out under identical conditions as described above for target biomarker (hErbB2/Her2) protein. Here, three different samples, such as;

(a) Blind serum samples containing target biomarker protein, where at least two different hErbB2/Her2 protein concentrations in replicates was used as positive controls.

(b) Serum samples spiked with three distinct non-specific proteins as negative controls at different concentrations, such as:

(i) Epidermal growth factor receptor-1 (EGFR1) at 5 and 2.5 ng mL$^{-1}$. EGFR1 is selected because of its structural similarity with human-ErbB2/Her2 protein, both belonged to same family of proteins.

Other non-specific proteins tested were;

(ii) Human fibroblast growth factor (FGF) at varying concentrations, such as 1, 5 and 10 ng mL$^{-1}$. FGF was used as a non-specific protein because it is a co-existing protein in serum.

(iii) Serum sample spiked with bovine serum albumin (BSA) protein was used as a second negative control.

The PoC biochip specificity and functionality tested using the unknown target samples were calculated and validated by matching with the expected levels.

Figure 9A:
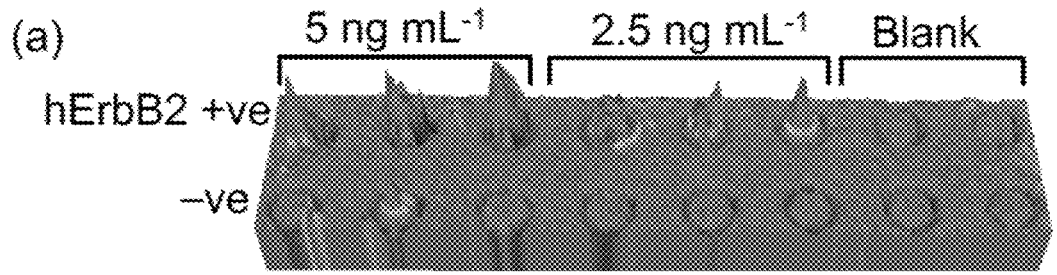
FIG. 9A shows a 3D profile generated from immuno-optomagnetic PoC biochip platform shown in the following FIG. 9B.
Figure 9B:
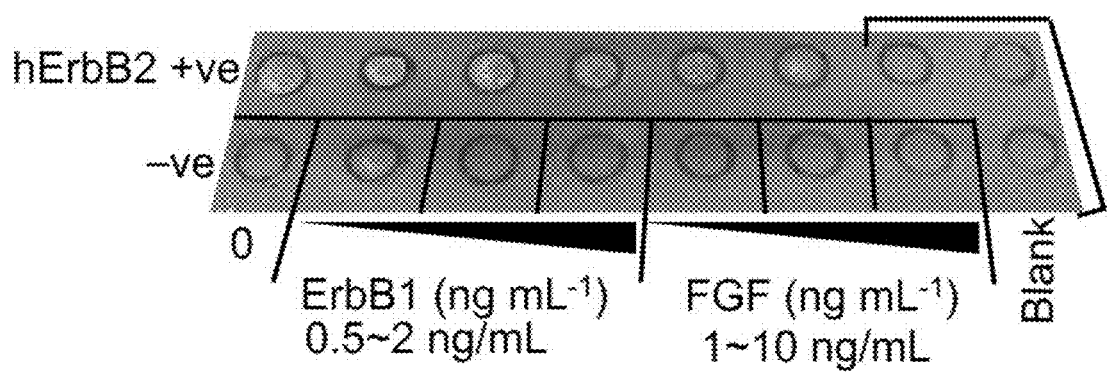
FIG. 9B shows a real image of immuno-optomagnetic PoC biochip post incubation for specificity tests using positive and negative controls, such as hErbB2/Her2 and non-specific proteins (EGFR1 and FGF), respectively. For positive controls, the serum samples containing hErbB2/Her2 were blinded and the diagnosis signal generated was confirmed for expected concentrations.

FIGS. 9A-9B show results of specificity tests carried out using PoC biochip and immuno-optomagnetic nanocrystals (MQDs-Ab2) under standard assay conditions similar to that used for detection of main model analyte (hErbB2/Her2 protein). Specificity tests revealed successful detection of analyte hErbB2/Her2 protein in blind serum sample corresponding to 2.5 and 5 ng mL$^{-1}$ that matched to the expected levels.

It is evident from FIGS. 9A-9B that the immuno-optomagnetic PoC tests did not show cross reactivity with any of the nonspecific proteins tested, such as for eg., but not limited structurally similar EGFR (ErbB1) protein or FGF or BSA proteins, indicating that the PoC biochip in conjunction with immuno-optomagnetic quantum dot nanocrystals (MQDs-Ab2) provided high specificity to target analyte (hErbB2/Her2 protein) with a limit-of-detection in the range 0.62 to 10 ng mL$^{-1}$, most suitable for breast cancer diagnosis at patient bedside, hospitals or homes. The target analyte or sample described in present invention refers to models, which is not limited to biomarker protein or serum, rather it is applicable to a whole range of target analyte or sample solution, such as other biomarkers, bacteria, virus, nucleic acids (DNA/RNA), drugs, chemicals, pesticides, or environmental agents.

REFERENCES CITED IN THE DESCRIPTION

This list of references cited by the applicant is for the reader's convenience only. It does not form part of the patent document. Even though great care has been taken in compiling the references, errors or omissions cannot be excluded in this regard.

Non-Patent Literature Cited in the Description

1. Panwar, V, et al., *PEGylated magnetic nanoparticles (PEG@Fe$_3$O$_4$) as cost effective alternative for oxidative cyanation of tertiary amines via CH activation*. Applied Catalysis A: General, 2015. 498: p. 25-31.

2. Bae, W. K., et al., *Single-step synthesis of quantum dots with chemical composition gradients*. Chemistry of Materials, 2008. 20(2): p. 531-539.
3. Zhang, Y J., A. M. Schnoes, and A. R. Clapp, *Dithiocarbamates as Capping Ligands for Water-Soluble Quantum Dots*. Acs Applied Materials & Interfaces, 2010. 2(11): p. 3384-3395.
4. Dubois, F., et al., *A versatile strategy for quantum dot ligand exchange*. Journal of the American Chemical Society, 2007. 129(3): p. 482-483.
5. Wang, Y, et al., *Stimulated emission and lasing from CdSe/CdS/ZnS core-multi-shell quantum dots by simultaneous three photon absorption*. Adv Mater, 2014. 26(18): p. 2954-61.
6. Sasaki, T., et al., Serum HER2 levels and HER2 status in tumor cells in advanced gastric cancer patients. Japanese Journal of Clinical Oncology, 2014. 45(1): p. 43-48.
7. Fehm, T., et al., Determination of HER2 status using both serum HER2 levels and circulating tumor cells in patients with recurrent breast cancer whose primary tumor was HER2 negative or of unknown HER2 status. Breast Cancer Research, 2007. 9(5): p. R74.
8. Fabricio, A. S. C., et al., Shed HER2 surrogacy evaluation in primary breast cancer patients: a study assessing tumor tissue HER2 expression at both extracellular and intracellular levels. Scandinavian Journal of Clinical and Laboratory Investigation, 2019. 79(4): p. 260-267.
9. Arsalani, S., et al., Magnetic $Fe_3O_4$ nanoparticles coated by natural rubber latex as MRI contrast agent. Journal of Magnetism and Magnetic Materials, 2019. 475: p. 458-464. 10. (WHO), W.H.O., Breast cancer. WHO, 2018: p. https://www.who.int/cancer/prevention/diagnosisscreening/breast-cancer/en/.
11. Veeraraghavan, J., et al., A combinatorial biomarker predicts pathologic complete response to neoadjuvant lapatinib and trastuzumab without chemotherapy in patients with HER2+ breast cancer. Annals of Oncology, 2019. 30(6): p. 927-933.
12. Lee, M. H., et al., The Significance of Serum HER2 Levels at Diagnosis on Intrinsic Subtype-Specific Outcome of Operable Breast Cancer Patients. PloS one, 2016. 11(10): p. e0163370-e0163370.
13. Tchou, J., et al., Monitoring serum HER2 levels in breast cancer patients. SpringerPlus, 2015. 4(1): p. 237.
14. Bhusari, P., et al., Development of Lu-177-trastuzumab for radioimmunotherapy of HER2 expressing breast cancer and its feasibility assessment in breast cancer patients. International journal of cancer, 2017. 140(4): p. 938-947.
15. Luoh, S.-W., et al., GRB7 dependent proliferation of basal-like, HER-2 positive human breast cancer cell lines is mediated in part by HER-1 signaling. Molecular Carcinogenesis, 2019. 58(5): p. 699-707.
16. Iqbal, N. and N. Iqbal, Human Epidermal Growth Factor Receptor 2 (HER2) in Cancers: Overexpression and Therapeutic Implications. Molecular biology international, 2014. 2014: p. 852748-852748.
17. English, D. P, D. M. Roque, and A. D. Santin, HER2 Expression Beyond Breast Cancer: Therapeutic Implications for Gynecologic Malignancies. Molecular Diagnosis & Therapy, 2013. 17(2): p. 85-99.
18. Chen, Z., et al., Ultrasensitive Sensor Using Quantum Dots-Doped Polystyrene Nanospheres for Clinical Diagnostics of Low-Volume Serum Samples. Analytical Chemistry, 2019. 91(9): p. 5777-5785.
19. Qiu, X., et al., Nanobodies and Antibodies for Duplexed EGFR/HER2 Immunoassays Using Terbium-to-Quantum Dot FRET. Chemistry of Materials, 2016. 28(22): p. 8256-8267.
20. Tyrakowski, C. M. and P. T. Snee, Ratiometric CdSe/ZnS Quantum Dot Protein Sensor. Analytical Chemistry, 2014. 86(5): p. 2380-2386.
21. Bakalova, R., et al., Quantum Dot-Based Western Blot Technology for Ultrasensitive Detection of Tracer Proteins. Journal of the American Chemical Society, 2005. 127(26): p. 9328-9329.
22. Bilan, R., et al., Quantum-dot-based suspension microarray for multiplex detection of lung cancer markers: preclinical validation and comparison with the Luminex) (MAP®) system. Scientific Reports, 2017. 7: p. 44668.
23. Bilan, R. S., et al., Engineering of Optically Encoded Microbeads with FRET-Free Spatially Separated Quantum-Dot Layers for Multiplexed Assays. Chem Phys Chem, 2017. 18(8): p. 970-979.
24. Anfossi, L., et al., A lateral flow immunoassay for straightforward determination of fumonisin mycotoxins based on the quenching of the fluorescence of CdSe/ZnS quantum dots by gold and silver nanoparticles. Microchimica Acta, 2018. 185(2): p. 94.
25. Lin, Z., et al., Optical transformation of a CdTe quantum dot-based paper sensor for a visual fluorescence immunoassay induced by dissolved silver ions. Journal of Materials Chemistry B, 2017. 5(4): p. 826-833.
26. Qiu, Z., J. Shu, and D. Tang, Bioresponsive Release System for Visual Fluorescence Detection of Carcinoembryonic Antigen from Mesoporous Silica Nanocontainers Mediated Optical Color on Quantum Dot-Enzyme-Impregnated Paper. Analytical Chemistry, 2017. 89(9): p. 5152-5160.
27. Miyashita, M., et al., Quantitative diagnosis of HER2 protein expressing breast cancer by single-particle quantum dot imaging. Cancer Medicine, 2016. 5(10): p. 2813-2824.
28. Wang, S., et al., Quantitative detection of the tumor-associated antigen large external antigen in colorectal cancer tissues and cells using quantum dot probe. International Journal of Nanomedicine, 2016. 11: p. 235-247.
29. Yang, X. Q., et al., Quantum dot-based quantitative immunofluorescence detection and spectrum analysis of epidermal growth factor receptor in breast cancer tissue arrays. International Journal of Nanomedicine, 2011. 6: p. 2265-2273.
30. Hu, Z. L., et al., Biomarker quantification by multiplexed quantum dot technology for predicting lymph node metastasis and prognosis in head and neck cancer. Oncotarget, 2016. 7(28): p. 44676-44685.
31. Hu, M., et al., Ultrasensitive, Multiplexed Detection of Cancer Biomarkers Directly in Serum by Using a Quantum Dot-Based Microfluidic Protein Chip. ACS Nano, 2010. 4(1): p. 488-494.
32. Zhang, L.-J., et al., Quantum Dot Based Biotracking and Biodetection. Analytical Chemistry, 2019. 91(1): p. 532-547.
33. Shen, H., A. M. Jawaid, and P T. Snee, Poly(ethylene glycol) Carbodiimide Coupling Reagents for the Biological and Chemical Functionalization of Water-Soluble Nanoparticles. ACS Nano, 2009. 3(4): p. 915-923.
34. Snee, P. T., The Role of Colloidal Stability and Charge in Functionalization of Aqueous Quantum Dots. Accounts of Chemical Research, 2018. 51(11): p. 2949-2956.

35. Mahajan, K. D., et al., Magnetic quantum dots in biotechnology—synthesis and applications. Biotechnology Journal, 2013. 8(12): p. 1424-1434.
36. Kim, C., G. Hoffmann, and P. C. Searson, Integrated Magnetic Bead-Quantum Dot Immunoassay for Malaria Detection. ACS Sensors, 2017. 2(6): p. 766-772.
37. Chen, Z. and M. Lu, Novel electrochemical immunoassay for human IgG1 using metal sulfide quantum dot-doped bovine serum albumin microspheres on antibody-functionalized magnetic beads. Anal Chim Acta, 2017. 979: p. 24-30.
38. Gazouli, M., et al., Development of a quantum-dot-labelled magnetic immunoassay method for circulating colorectal cancer cell detection. World J Gastroenterol, 2012. 18(32): p. 4419-26.
39. Kim, C., G. Hoffmann, and P C. Searson, Integrated Magnetic Bead-Quantum Dot Immunoassay for Malaria Detection. ACS Sens, 2017. 2(6): p. 766-772.
40. Tang, D., et al., Multiplexed electrochemical immunoassay of biomarkers using metal sulfide quantum dot nanolabels and trifunctionalized magnetic beads. Biosens Bioelectron, 2013. 46: p. 37-43.
41. Wang, H., et al., Rapid, sensitive, and simultaneous detection of three foodborne pathogens using magnetic nanobead-based immunoseparation and quantum dot-based multiplex immunoassay. J Food Prot, 2011. 74(12): p. 2039-47.
42. Yu, F., et al., Magnetic immunoassay using CdSe/ZnS quantum dots as fluorescent probes to detect the level of DNA methyltransferase 1 in human serum sample. Int J Nanomedicine, 2018. 13: p. 429-437.
43. Kim, C. and P C. Searson, Magnetic bead-quantum dot assay for detection of a biomarker for traumatic brain injury. Nanoscale, 2015. 7(42): p. 17820-6.
44. Gupta, A. K. and M. Gupta, Synthesis and surface engineering of iron oxide nanoparticles for biomedical applications. Biomaterials, 2005. 26(18): p. 3995-4021.
45. Ma, Q., et al., Multilayered, core/shell nanoprobes based on magnetic ferric oxide particles and quantum dots for multimodality imaging of breast cancer tumors. Biomaterials, 2012. 33(33): p. 8486-8494.
46. Ruan, G., et al., Simultaneous magnetic manipulation and fluorescent tracking of multiple individual hybrid nanostructures. Nano letters, 2010. 10(6): p. 2220-2224.
47. Mahajan, K. D., et al., A MagDot-nanoconveyor assay detects and isolates molecular biomarkers. Chemical Engineering Progress, 2012. 108: p. 41.
48. Tuerk, C. and L. Gold, Systematic evolution of ligands by exponential enrichment: RNA ligands to bacteriophage T4 DNA polymerase. science, 1990. 249(4968): p. 505-510.
49. Rong, Z., et al., Dual-color magnetic-quantum dot nanobeads as versatile fluorescent probes in test strip for simultaneous point-of-care detection of free and complexed prostate-specific antigen. Biosens Bioelectron, 2019. 145: p. 111719.

What is claimed is:

1. A method for detecting and quantifying of a target analyte in a test sample, comprising the steps of:
   i. providing a point-of-care (PoC) borofloat chip platform containing chambers functionalized with a first analyte specific reagent, wherein the first analyte specific reagent specifically binds the target analyte,
   ii. providing 3-10 nm sized multi-colored CdSe/CdS/ZnS core-shell-shell quantum dot (QD) nanocrystals by mixing of 3-10 nm sized pure single colored red and green QD nanocrystals, wherein QD nanocrystals comprise free —COOH functionality,
   iii. providing 50-100 nm sized optomagnetic quantum dot (MQD) nanocrystals by coating the 3-10 nm sized multi-colored CdSe/CdS/ZnS QD nanocrystals with 7-12 nm sized magnetic nanoparticles,
   iv. providing a plurality of functionalized optomagnetic MQD nanocrystals by functionalization of the magnetic nanoparticle coated QD nanocrystals obtained in step iii with a second analyte specific reagent, wherein the second analyte specific reagent is capable of binding to the analyte,
   v. contacting the plurality of functionalized optomagnetic MQD nanocrystals obtained is step iv with the test sample and forming MQD nanocrystals-second analyte specific reagent-target analyte complex,
   vi. separating the MQD nanocrystals-second analyte specific reagent-target analyte complex obtained in step v from test sample using an external magnet,
   vii. loading the separated MQD nanocrystals-second analyte specific reagent-target analyte complex obtained in step vi onto the PoC borofloat chip platform of step i and forming a sandwich complex between the first analyte specific reagent of the PoC borofloat chip platform and the MQD nanocrystals-second analyte specific reagent-target analyte complex,
   viii. exposing the PoC borofloat chip having the sandwich complex from step vii to UV light and detecting and/or quantifying the target analyte from fluorescence signal;
   wherein said first analyte specific reagent and the second analyte specific reagent specifically binds the same target analyte but each binds to different sides or different epitopes of the same analyte.

2. The method according to claim 1, wherein the target analyte is protein biomarkers, biomolecule, pathogenic bacteria, virus, nucleic acids (DNA/RNA), environmental contaminant, chemical, pesticide or drug.

3. The method according to claim 2, wherein the protein biomarker is human-ErbB2/Her2.

4. The method according to claim 1, wherein the test sample is biological fluids; such as serum, blood, urine, saliva, sweat, CSF or interstitial fluid; water or environmental samples.

5. The method according to claim 1, wherein the analyte specific reagent is antibody, receptor, DNA/RNA probe, chemical, drug, bacteria or virus.

6. The method according to claim 1, wherein the first analyte specific reagent is a primary antibody and the second analyte specific reagent is a second antibody.

7. The method according to claim 1, wherein a UV-excited fluorescence emission signal from the MQD nanocrystals-second analyte specific reagent-target analyte complex is detected directly with a naked eye.

8. The method according to claim 1, wherein a fluorescence signal from the MQD nanocrystals-second analyte specific reagent-target analyte complex is measured quantitatively using a smartphone camera equipped with an RGB (red, green and blue) profiling algorithm.

9. The method according to claim 1, wherein the MQD nanocrystals of step iv capture target analytes within 15-30 min.

* * * * *